US005731180A

United States Patent [19]
Dietrich

[11] Patent Number: 5,731,180
[45] Date of Patent: Mar. 24, 1998

[54] IMIDAZOLINONE RESISTANT AHAS MUTANTS

[75] Inventor: Gabriele Elfriede Dietrich, Rocky Hill, N.J.

[73] Assignee: American Cyanamid Company, Wayne, N.J.

[21] Appl. No.: 737,851

[22] Filed: Jul. 31, 1991

[51] Int. Cl.$^6$ .......... C12N 15/63; C12N 15/29; C12N 5/10; C12N 1/21

[52] U.S. Cl. .......... 435/172.3; 435/172.1; 435/183; 435/320.1; 435/6; 435/7.6; 435/240.1; 435/240.4; 435/252.3; 435/69.1; 435/70.1; 435/71.1; 536/23.2; 536/23.6; 530/376

[58] Field of Search .......... 800/205, 250; 435/172.3, 172.1, 240.4, 252.3, 240.1, 6, 7.6, 183, 320.1, 69.1, 70.1, 71.1; 530/376; 536/23.6, 23.2

[56] References Cited

U.S. PATENT DOCUMENTS 4,761,373 8/1988 Anderson et al. .......... 435/172.3

OTHER PUBLICATIONS

Anderson et al. Genome, vol. 31 (1989) pp. 994–999.
Jen et al. (Abstract) J. Cellular Biochem., vol. 14E (supplement) (1990) p. 302.
Wiersma et al. Mol. Gen. Genet., vol. 219 (1989) pp. 413–420.
Lesser, W.H., ed., Animal Patents, N.Y., Stockton Press, 1989, p. 159.
Haughn, G. et al., "A mutation causing imidazolinone resistance . . . " Plant Physiology, vol. 92, (Apr., 1990), pp. 1081–1085.
Sathasivan et al., "Nucleotide sequence of a mutant acetolacrane synthase gene . . . ", Nucleic Acids Research, vol. 18 (Apr. 1990) p. 2188.
Haughn et al., "Transformatioin with a mutant *Arabidopsis* acetoacetate synthease gene . . . ", Mol. Gen. Genet., vol. 211 (1988) pp. 266–271.

*Primary Examiner*—Charles C.P. Rories
*Attorney, Agent, or Firm*—Darryl L. Webster; Alan M. Gordon; Gale F. Matthews

[57] ABSTRACT

The present invention relates to monocot genes encoding a mutant AHAS enzyme that is specifically resistant to imidazolinone herbicides. Exemplary of these genes are corn DNA sequences which encode an amino acid substitution at position 621 of the wild-type AHAS enzyme. The mutant gene can be used to transform other plants to herbicide resistance; in this regard, the invention also provides host cells and vectors containing the gene, which cells and vectors are useful in the transformation process.

8 Claims, 29 Drawing Sheets

- ⊤ SalI
- ☐ XhoI
- ◇ HindIII
- ○ XbaI
- ● ClaI
- ■ PstI

W22/1A and B73/7-4 sequence:   5'TAGTG3'
                                3'ATCTG5'

X112/8A sequence:   5'TAATG3'
                    3'ATTAC5'

FIG. 6A

```
         40            50            60            70            80            90
          *             *             *             *             *             *
ATG GCC ACC GCC GCC GCG TCT ACC GCG CTC ACT GGC GCC ACT GCT ACC GCG
Met Ala Thr Ala Ala Ala Ser Thr Ala Leu Thr Gly Ala Thr Thr Ala Ala 100           110           120           130           140
          *             *             *             *             *
CCC AAG GCG AGG CGC CGG GCG CAC CTC CTG GCC ACC CGC CGC GCC CTC GCC GCG
Pro Lys Ala Arg Arg Arg Ala His Leu Leu Ala Thr Arg Arg Ala Leu Ala Ala 150           160           170           180           190
          *             *             *             *             *
CCC ATC AGG TGC TCA GCG GCG TCA CCC GCC ATG CCG ATG GCT CCC CCG GCC ACC
Pro Ile Arg Cys Ser Ala Ala Ser Pro Ala Met Pro Met Ala Pro Pro Ala Thr 200           210           220           230           240           250
          *             *             *             *             *             *
CCG CTC CGG CCG TGG GGC CCC ACC GAT CCC CGC AAG GGC GCC GAC ATC CTC GTC
Pro Leu Arg Pro Trp Gly Pro Thr Asp Pro Arg Lys Gly Ala Asp Ile Leu Val 260           270           280           290           300
          *             *             *             *             *
GAG TCC CTC GAG CGC TGC GGC GTC GTC TTC GCC TAC CCC GGC GGC GCG
Glu Ser Leu Glu Arg Cys Gly Val Arg Asp Val Phe Ala Tyr Pro Gly Gly Ala
```

FIG. 6B

```
310         320         330         340         350         360
 *           *           *           *           *           *
TCC ATG GAG ATC CAC CAG GCA CTC ACC CGC TCC CCC GTC ATC GCC AAC CAC CTC
Ser Met Glu Ile His Gln Ala Leu Thr Arg Ser Pro Val Ile Ala Asn His Leu 370         380         390         400         410
 *           *           *           *           *
TTC CGC CAC GAG CAA GGG GAG GCC TTT GCG GCC TCC GGC TAC GCG GCG TCC TCG
Phe Arg His Glu Gln Gly Glu Ala Phe Ala Ala Ser Gly Tyr Ala Ala Ser Ser 420         430         440         450         460
 *           *           *           *           *
GGC CGC GTC GGC GTC TGC ATC GCC ACC TCC GGC CCC GGC GCC ACC AAC CTT GTC
Gly Arg Val Gly Val Cys Ile Ala Thr Ser Gly Pro Gly Ala Thr Asn Leu Val 470         480         490         500         510         520
 *           *           *           *           *           *
TCC GCG CTC GCC GAC GCG CTG CTC GAT TCC GTC CCC ATG GTC GCC ATC ACG GGA
Ser Ala Leu Ala Asp Ala Leu Leu Asp Ser Val Pro Met Val Ala Ile Thr Gly
```

FIG. 6C

```
      530                540                550                560                570
       *                  *                  *                  *                  *
CAG GTG CCG CGA CGC ATG ATT GGC ACC GAC GCC TTC CAG GAG ACG CCC ATC GTC
Gln Val Pro Arg Arg Met Ile Gly Thr Asp Ala Phe Gln Glu Thr Pro Ile Val 580                590                600                610                620                630
       *                  *                  *                  *                  *                  *
GAG GTC ACC CGC TCC ATC ACC AAG CAC AAC TAC CTG GTC CTC GAC GTC GAC GAC
Glu Val Thr Arg Ser Ile Thr Lys His Asn Tyr Leu Val Leu Asp Val Asp Asp 640                650                660                670                680
       *                  *                  *                  *                  *
ATC CCC CGC GTC GTG CAG GAG GCT TTC CTC GCC TCC TCT GGT CGA CCG GGG
Ile Pro Arg Val Val Gln Glu Ala Phe Phe Leu Ala Ser Ser Gly Arg Pro Gly 690                700                710                720                730
       *                  *                  *                  *                  *
CCG GTG CTT GTC GAC ATC CCC AAG GAC ATC CAG CAG ATG GCG GTG CCT GTC
Pro Val Leu Val Asp Ile Pro Lys Asp Ile Gln Gln Met Ala Val Pro Val
```

FIG. 6D

```
740        750        760        770        780        790
 *          *          *          *          *          *
TGG GAC AAG CCC ATG AGT CTG CCT GGG TAC ATT GCG CGC CTT CCC AAG CCC CCT
Trp Asp Lys Pro Met Ser Leu Pro Gly Tyr Ile Ala Arg Leu Pro Lys Pro Pro 800        810        820        830        840
            *          *          *          *          *
GCG ACT GAG TTG CTT GGC GAG CAG GTG CTG CGT CTT GTT GGT GAA TCC CGG CGC CCT
Ala Thr Glu Leu Leu Gly Glu Gln Val Leu Arg Leu Val Gly Glu Ser Arg Arg Pro 850        860        870        880        890        900
 *          *          *          *          *          *
GTT CTT TAT GTT GGC GGT GCG TGC GCA TCT GGT GAG GAG TTG CGA CGC TTT
Val Leu Tyr Val Gly Gly Ala Cys Ala Ser Gly Glu Glu Leu Arg Arg Phe 910        920        930        940        950
            *          *          *          *          *
GTG GAG CTG ACT GGA ATC CCG GTC ACA ACT CTT ATG GGC CTC GGC AAC TTC
Val Glu Leu Thr Gly Ile Pro Val Thr Thr Leu Met Gly Leu Gly Asn Phe
```

FIG. 6E

```
       960            970            980            990            1000
        *              *              *              *              *
CCC AGC GAC GAC CCA CTG TCT CTG CGC ATG CTA GGT ATG CAT GGC ACG GTG TAT
Pro Ser Asp Asp Pro Leu Ser Leu Arg Met Leu Gly Met His Gly Thr Val Tyr 1010           1020           1030           1040           1050           1060
        *              *              *              *              *              *
GCA AAT TAT GCA GTG GAT AAG GCC GAT CTG TTG CTT GCA CTT GGT GTG CGG TTT
Ala Asn Tyr Ala Val Asp Lys Ala Asp Leu Leu Leu Ala Leu Gly Val Arg Phe 1070           1080           1090           1100           1110
        *              *              *              *              *
GAT GAT CGT GTG ACA GGG AAG ATT GAG GCT TTT GCA AGC AGG GCT AAG ATT GTG
Asp Asp Arg Val Thr Gly Lys Ile Glu Ala Phe Ala Ser Arg Ala Lys Ile Val 1120           1130           1140           1150           1160           1170
        *              *              *              *              *              *
CAC GTT GAT ATT GAT CCG GCT GAG ATT GGC AAG AAC AAG CAG CCA CAT GTG TCC
His Val Asp Ile Asp Pro Ala Glu Ile Gly Lys Asn Lys Gln Pro His Val Ser
```

FIG. 6F

```
      1180          1190          1200          1210          1220
       *             *             *             *             *
ATC TGT GCA GAT GTT AAG CTT GCT TTG CAG GGC ATG AAT GCT CTT CTT GAA GGA
Ile Cys Ala Asp Val Lys Leu Ala Leu Gln Gly Met Asn Ala Leu Leu Glu Gly 1230          1240          1250          1260          1270
       *             *             *             *             *
AGC ACA TCA AAG AAG AGC TTT GAC TTT GGC TCA TGG AAC GAT GAG TTG GAT CAG
Ser Thr Ser Lys Lys Ser Phe Asp Phe Gly Ser Trp Asn Asp Glu Leu Asp Gln 1280          1290          1300          1310          1320          1330
 *             *             *             *             *             *
CAG AAG AGG GAA TTC CCC CTT GGG TAT AAA ACA TCT AAT GAG ATC CAG CCA
Gln Lys Arg Glu Phe Pro Leu Gly Tyr Lys Thr Ser Asn Glu Ile Gln Pro 1340          1350          1360          1370          1380
       *             *             *             *             *
CAA TAT GCT ATT CAG GTT CTT GAT GAG CTG ACG AAA GGC GAG GCC ATC ATC GGC
Gln Tyr Ala Ile Gln Val Leu Asp Glu Leu Thr Lys Gly Glu Ala Ile Ile Gly
```

FIG. 6G

```
           1390      1400      1410      1420      1430      1440
            *         *         *         *         *         *
           ACA GGT GTT GGG CAG CAC CAG ATG TGG GCG GCA CAG TAC TAC ACT TAC AAG CGG
           Thr Gly Val Gly Gln His Gln Met Trp Ala Ala Gln Tyr Tyr Thr Tyr Lys Arg 1450      1460      1470      1480      1490
            *         *         *         *         *
           CCA AGG CAG TGG TTG TCT TCA GCT GTT CTT GGG GCT ATG GGA TTT GGT TTG CCG
           Pro Arg Gln Trp Leu Ser Ser Ala Val Leu Gly Ala Met Gly Phe Gly Leu Pro 1500      1510      1520      1530      1540
            *         *         *         *         *
           GCT GCT GCT GGT GCT TCT GTG GCC AAC CCA GGT GTT ACT GTT GAC ATC GAT
           Ala Ala Ala Gly Ala Ser Val Ala Asn Pro Gly Val Thr Val Asp Ile Asp 1550      1560      1570      1580      1590      1600
            *         *         *         *         *         *
           GGA GAT GGT AGC TTT CTC ATG AAC GTT CAG GAG CTA GCT ATG ATC CGA ATT GAG
           Gly Asp Gly Ser Phe Leu Met Asn Val Gln Glu Leu Ala Met Ile Arg Ile Glu
```

FIG. 6H

```
         1610            1620            1630            1640            1650
          *               *               *               *               *
AAC CTC CCG GTG AAG GTC TTT GTG CTA AAC AAC CAG CAC CTG GGG ATG GTG GTG
Asn Leu Pro Val Lys Val Phe Val Leu Asn Asn Gln His Leu Gly Met Val Val 1660            1670            1680            1690            1700            1710
          *               *               *               *               *               *
CAG TGG GAG GAC AGG TTC TAT AAG GCC AAC AGA GCG CAC ACA TAC TTG GGA AAC
Gln Trp Glu Asp Arg Phe Tyr Lys Ala Asn Arg Ala His Thr Tyr Leu Gly Asn 1720            1730            1740            1750            1760
          *               *               *               *               *
CCA GAG AAT GAA AGT GAG ATA TAT CCA GAT TTC GTG ACG ATC GCC AAA GGG TTC
Pro Glu Asn Glu Ser Glu Ile Tyr Pro Asp Phe Val Thr Ile Ala Lys Gly Phe 1770            1780            1790            1800            1810
          *               *               *               *               *
AAC ATT CCA GCG GTC CGT GTG ACA AAG AAG AAC GAA GTC CGC GCA ATA AAG
Asn Ile Pro Ala Val Arg Val Thr Lys Lys Asn Glu Val Arg Ala Ala Ile Lys
```

FIG. 6I

```
1820        1830        1840        1850        1860        1870
 *           *           *           *           *           *
AAG ATG CTC GAG ACT CCA GGG CCG TAC CTC TTG GAT ATA ATC GTC CCA CAC CAG
Lys Met Leu Glu Thr Pro Gly Pro Tyr Leu Leu Asp Ile Ile Val Pro His Gln 1880        1890        1900        1910        1920
            *           *           *           *           *
GAG CAT GTG TTG CCT ATG ATC CCT AAT GGT GGG GCT TTC AAG GAT ATG ATC CTG
Glu His Val Leu Pro Met Ile Pro Asn Gly Gly Ala Phe Lys Asp Met Ile Leu 1930        1940        1950        1960
 *           *           *           *
GAT GGT GAT GGC AGG ACT GTG TAC TGATC TAAAA TCCAG CAAG
Asp Gly Asp Gly Arg Thr Val Tyr
```

FIG. 7A

```
                       10         20         30         40         50         60
XI12/8A     AACCC TCGCG CCGCC TCCGA GACAG CCGCC GCAAC CATGG CCACC GCCGC CGCCG CGTCT
W22/1A      AACCC TCGCG CCGCC TCCGA GACAG CCGCC GCAAC CATGG CCACC GCCGC CGCCG CGTCT
            11111 11111 11111 11111 11111 11111 11111 11111 11111 11111 11111 11111
B73/7-4     AACCC TCGCG CCGCC TCCGA GACAG CCGCC GCAAC CATGG CCACC GCCGC CGCCG CGTCT
            11111 11111 11111 11111 11111 11111 11111 11111 11111 11111 11111 11111
XI12/8A     AACCC TCGCG CCGCC TCCGA GACAG CCGCC GCAAC CATGG CCACC GCCGC CGCCG CGTCT 70         80         90        100        110        120
XI12/8A     ACCGC GCTCA CTGGC GCCAC TACCG CTGCG CCCAA GGCGA GGCGC CGGGC GCACC TCCTG
W22/1A      ACCGC GCTCA CTGGC GCCAC TACCG CTGCG CCCAA GGCGA GGCGC CGGGC GCACC TCCTG
            11111 11111 11111 11111 11111 11111 11111 11111 11111 11111 11111 11111
B73/7-4     ACCGC GCTCA CTGGC GCCAC TACCG CTGCG CCCAA GGCGA GGCGC CGGGC GCACC TCCTG
            11111 11111 11111 11111 11111 11111 11111 11111 11111 11111 11111 11111
XI12/8A     ACCGC GCTCA CTGGC GCCAC TACCG CTGCG CCCAA GGCGA GGCGC CGGGC GCACC TCCTG 130        140        150        160        170        180
XI12/8A     GCCAC CCGCC GCGCC CTCGC CGGCG CCATC AGGTG CTCAG CGGCG TCACC CGCCA TGCCG
W22/1A      GCCAC CCGCC GCGCC CTCGC CGGCG CCATC AGGTG CTCAG CGGCG TCACC CGCCA TGCCG
            11111 11111 11111 11111 11111 11111 11111 11111 11111 11111 11111 11111
B73/7-4     GCCAC CCGCC GCGCC CTCGC CGGCG CCATC AGGTG CTCAG CGGCG TCACC CGCCA TGCCG
            11111 11111 11111 11111 11111 11111 11111 11111 11111 11111 11111 11111
            GCCAC CCGCC GCGCC CTCGC CGGCG CCATC AGGTG CTCAG CGGCG TCACC CGCCA TGCCG
```

FIG. 7B

```
              190         200         210         220         230         240
XI12/8A  ATGGC TCCCC CGGCC ACCCC GCTCC GGCCG TGGGG CCCCA CCGAT CCCCG CAAGG GCGCC
W22/1A   ATGGC TCCCC CGGCC ACCCC GCTCC GGCCG TGGGG CCCCA CCGAT CCCCG CAAGG GCGCC
         11111 11111 11111 11111 11111 11111 11111 11111 11111 11111 11111 11111
B73/7-4  ATGGC TCCCC CGGCC GCCAC GCTCC GGCCG TGGGG CCCCA CCGAg CCCCG CAAGG GtGCt
         11111 11111 11111 11111 11111 11111 11111 11111 11111 11111 11111 11111
XI12/8A  ATGGC TCCCC CGGCC ACCCC GCTCC GGCCG TGGGG CCCCA CCGAT CCCCG CAAGG GCGCC 250         260         270         280         290         300
XI12/8A  GACAT CCTCG TCGAG TCCCT CGAGC GCTGC CCGCG CCGGG ACGTC TTCGC CTACC CCGGC
W22/1A   GACAT CCTCG TCGAG TCCCT CGAGC GCTGC CCGCG CCGGT ACGTC TTCGC CTACC CCGGC
         11111 11111 11111 11111 11111 11111 11111 11111 11111 11111 11111 11111
B73/7-4  GACAT CCTCG TCGAG TCCCT CGAGC GCTGC CCGCG CCGGT ACGTC TTCGC CTACC CCGGC
         11111 11111 11111 11111 11111 11111 11111 11111 11111 11111 11111 11111
XI12/8A  GACAT CCTCG TCGAG TCCCT CGAGC GCTGC CCGCG CCGGT ACGTC TTCGC CTACC CCGGC 310         320         330         340         350         360
XI12/8A  GGCGC GTCCA TGGAG ATCCA CCAGG CACTC ACCCG CTCCC CCGTC ATCGC CAACC ACCTC
W22/1A   GGCGC GTCCA TGGAG ATCCA CCAGG CACTC ACCCG CTCCC CCGTC ATCGC CAACC ACCTC
         11111 11111 11111 11111 11111 11111 11111 11111 11111 11111 11111 11111
XB73/7-4 GGCGC GTCCA TGGAG ATCCA CCAGG CACTC ACCCG CTCCC CCGTC ATCGC CAACC ACCTC
         11111 11111 11111 11111 11111 11111 11111 11111 11111 11111 11111 11111
XI12/8A  GGCGC GTCCA TGGAG ATCCA CCAGG CACTC ACCCG CTCCC CCGTC ATCGC CAACC ACCTC
```

FIG. 7C

```
                  370         380         390         400         410         420
XI12/8A     TTCCG CCACG AGCAA GGGGA GGCCT TTGCG GCCTC ACGCG CGCTC CGGCT CTCGG GCCGC
W22/1A      TTCCG CCACG AGCAA GGGGA GGCCT TTGCG GCCTC ACGCG CGCTC CGGCT CTCGG GCCGC
            11111 11111 11111 11111 11111 11111 11111 11111 11111 11111 11111 11111
B73/7-4     TTCCG CCACG AGCAA GGGGA GGCCT TTGCc GCCTC ACGCG CGCTC CGGCT CTCGG GCCGC
            11111 11111 11111 11111 11111 11111 11111 11111 11111 11111 11111 11111
XI12/8A     TTCCG CCACG AGCAA GGGGA GGCCT TTGCG GCCTC ACGCG CGCTC CGGCT CTCGG GCCGC 430         440         450         460         470         480
XI12/8A     GTCGG CGTCT GCATC GCCAC CTCCG GCCCC CACCA ACCTT GTCTC CGCGC TCGCC
W22/1A      GTCGG CGTCT GCATC GCCAC CTCCG GCCCC CACCA ACCTT GTCTC CGCGC TCGCC
            11111 11111 11111 11111 11111 11111 11111 11111 11111 11111 11111
B73/7-4     GTCGG CGTCT GCATC GCCAC CTCCG GCCCC CACCA ACCTa GTCTC CGCGC TCGCC
            11111 11111 11111 11111 11111 11111 11111 11111 11111 11111 11111
XI12/8A     GTCGG CGTCT GCATC GCCAC CTCCG GCCCC CACCA ACCTT GTCTC CGCGC TCGCC 490         500         510         520         530         540
XI12/8A     GACGC GCTGC TCGAT TCCGT CCCCA TGGTC GCCAT CACGG GACAG GTGCC GCGAC GCATG
W22/1A      GACGC GCTGC TCGAT TCCGT CCCCA TGGTC GCCAT CACGG GACAG GTGCC GCGAC GCATG
            11111 11111 11111 11111 11111 11111 11111 11111 11111 11111 11111 11111
B73/7-4     GACGC GCTGC TCGAT TCCGT CCCCA TGGTC GCCAT CACGG GACAG GTGCC GCGAC GCATG
            11111 11111 11111 11111 11111 11111 11111 11111 11111 11111 11111 11111
XI12/8A     GACGC GCTGC TCGAT TCCGT CCCCA TGGTC GCCAT CACGG GACAG GTGCC GCGAC GCATG
```

FIG. 7D

|          |       | 550   |       |       |       | 560   |       |       |       | 570   |       |       |       | 580   |       |       |       | 590   |       |       |       | 600   |
|----------|-------|-------|-------|-------|-------|-------|-------|-------|-------|-------|-------|-------|-------|-------|-------|-------|-------|-------|-------|-------|-------|-------|
| XI12/8A  |       | ATTGG | CACCG | ACGCC | TTCCA | GGAGA | CGCCC | ATCGT | CGAGG | TCACC | CGCTC | CATCA | CCAAG |
| W22/1A   | ATTGG | CACCG | ACGCC | TTCCA | GGAGA | CGCCC | ATCGT | CGAGG | TCACC | CGCTC | CATCA | CCAAG |
|          | 11111 | 11111 | 11111 | 11111 | 11111 | 11111 | 11111 | 11111 | 11111 | 11111 | 11111 | 11111 |
| B73/7-4  | ATTGG | CACCG | ACGCC | TTCCA | GGAGA | CGCCC | ATCGT | CGAGG | TCACC | CGCTC | CATCA | CCAAG |
|          | 11111 | 11111 | 11111 | 11111 | 11111 | 11111 | 11111 | 11111 | 11111 | 11111 | 11111 | 11111 |
| XI12/8A  | ATTGG | CACCG | ACGCC | TTCCA | GGAGA | CGCCC | ATCGT | CGAGG | TCACC | CGCTC | CATCA | CCAAG |

|          |       | 610   |       |       |       | 620   |       |       |       | 630   |       |       |       | 640   |       |       |       | 650   |       |       |       | 660   |
|----------|-------|-------|-------|-------|-------|-------|-------|-------|-------|-------|-------|-------|-------|-------|-------|-------|-------|-------|-------|-------|-------|-------|
| XI12/8A  |       | CACAA | CTACC | TGGTC | CTCGA | CGTCG | ACGAC | ATCCC | CCGCG | TCGTG | CAGGA | GGCTT | TCTTC |
| W22/1A   | CACAA | CTACC | TGGTC | CTCGA | CGTCG | ACGAC | ATCCC | CCGCG | TCGTG | CAGGA | GGCTT | TCTTC |
|          | 11111 | 11111 | 11111 | 11111 | 11111 | 11111 | 11111 | 11111 | 11111 | 11111 | 11111 | 11111 |
| B73/7-4  | CACAA | CTACC | TGGTC | CTCGA | CGTCG | ACGAC | ATCCC | CCGCG | TCGTG | CAGGA | GGCTT | TCTTC |
|          | 11111 | 11111 | 11111 | 11111 | 11111 | 11111 | 11111 | 11111 | 11111 | 11111 | 11111 | 11111 |
| XI12/8A  | CACAA | CTACC | TGGTC | CTCGA | CGTCG | ACGAC | ATCCC | CCGCG | TCGTG | CAGGA | GGCTT | TCTTC |

|          |       | 670   |       |       |       | 680   |       |       |       | 690   |       |       |       | 700   |       |       |       | 710   |       |       |       | 720   |
|----------|-------|-------|-------|-------|-------|-------|-------|-------|-------|-------|-------|-------|-------|-------|-------|-------|-------|-------|-------|-------|-------|-------|
| XI12/8A  |       | CTCGC | CTCCT | CTGGT | CGACC | GGGGC | CGGTG | CTTGT | CGACA | TCCCC | AAGGA | CATCC | AGCAG |
| W22/1A   | CTCGC | CTCCT | CTGGT | CGACC | GGGGC | CGGTG | CTTGT | CGACA | TCCCC | AAGGA | CATCC | AGCAG |
|          | 11111 | 11111 | 11111 | 11111 | 11111 | 11111 | 11111 | 11111 | 11111 | 11111 | 11111 | 11111 |
| B73/7-4  | CTCGC | CTCCT | CTGGT | CGACC | aGGGC | CGGTG | CTTGT | CGACA | TCCCC | AAGGA | CATCC | AGCAG |
|          | 11111 | 11111 | 11111 | 11111 | 11111 | 11111 | 11111 | 11111 | 11111 | 11111 | 11111 | 11111 |
| XI12/8A  | CTCGC | CTCCT | CTGGT | CGACC | GGGGC | CGGTG | CTTGT | CGACA | TCCCC | AAGGA | CATCC | AGCAG |

FIG. 7E

```
                 730              740              750              760              770              780
XI12/8A   CAGAT GGCGG TGCCT GTCTG GGACA AGCCC ATGAG TCTGC CTGGG TACAT TGCGC GCCTT
W22/1A    CAGAT GGCGG TGCCT GTCTG GGACA AGCCC ATGAG TCTGC CTGGG TACAT TGCGC GCCTT
          11111 11111 11111 11111 11111 11111 11111 11111 11111 11111 11111 11111
B73/7-4   CAGAT GGCGG TGCCT GTCTG GGACA AGCCC ATGAG TCTGC CTGGG TACAT TGCGC GCCTT
          11111 11111 11111 11111 11111 11111 11111 11111 11111 11111 11111 11111
XI12/8A   CAGAT GGCGG TGCCT GTCTG GGACA AGCCC ATGAG TCTGC CTGGG TACAT TGCGC GCCTT 790              800              810              820              830              840
XI12/8A   CCCAA GCCCC CTGCG ACTGA GTTGC TTGAG CAGGT GCTGC GTCTT GTTGG TGAAT CCCGG
W22/1A    CCCAA GCCCC CTGCG ACTGA GTTGC TTGAG CAGGT GCTGC GTCTT GTTGG TGAAT CCCGG
          11111 11111 11111 11111 11111 11111 11111 11111 11111 11111 11111 11111
B73/7-4   CCCAA GCCCC CTGCG ACTGA GTTGC TTGAG CAGGT GCTGC GTCTT GTTGG TGAAT CCCGG
          11111 11111 11111 11111 11111 11111 11111 11111 11111 11111 11111 11111
XI12/8A   CCCAA GCCCC CTGCG ACTGA GTTGC TTGAG CAGGT GCTGC GTCTT GTTGG TGAAT CCCGG 850              860              870              880              890              900
                                    ^
XI12/8A   CGCCC TGTTC TTTAT GTTGG CGGTG GCTGC ATCTG GTGAG GAGTT GCGAC GCTTT
W22/1A    CGCCC TGTTC TTTAT GTTGG CGGTG GCTGC ATCTG GTGAG GAGTT GCGAC GCTTT
          11111 11111 11111 11111 11111 11111 11111 11111 11111 11111 11111
B73/7-4   CGCCC TGTTC TTTAT GTgGG CGGTG GCTGC ATCTG GTGAG GAGTT CgCGG GCTTT
          11111 11111 11111 11111 11111 11111 11111 11111 11111 11111 11111
XI12/8A   CGCCC TGTTC TTTAT GTTGG CGGTG GCTGC ATCTG GTGAG GAGTT GCGAC GCTTT
```

FIG. 7F

```
                910         920         930         940         950         960
XI12/8A
W22/1A      GTGGA GCTGA CTGGA ATCCC GGTCA CAACT ACTCT TATGG GCCTC GGCAA CTTCC CCAGC
            11111 11111 11111 11111 11111 11111 11111 11111 11111 11111 11111 11111
B73/7-4     GTGGA GCTGA CTGGA ATCCC GGTCA CAACT ACTCT TATGG GCCTC GGCAA CTTCC CCAGC
            11111 11111 11111 11111 11111 11111 11111 11111 11111 11111 11111 11111
XI12/8A     GTGGA GCTGA CTGGA ATCCC GGTCA CAACT ACTCT TATGG GCCTC GGCAA CTTCC CCAGC 970         980         990        1000        1010        1020
                                              >
XI12/8A     GACGA CCCAC TGTCT CTGCG CATGC TAGGT ATGCA TGGCA CGGTG TATGC AAATT ATGCA
W22/1A      GACGA CCCAC TGTCT CTGCG CATGC TAGGT ATGCA TGGCA CGGTG TATGC AAATT ATGCA
            11111 11111 11111 11111 11111 11111 11111 11111 11111 11111 11111 11111
B73/7-4     GACGA CCCAC TGTCT CTGCG CATGC TAGGT ATGCA TGGgA CGGTG TATGC AAATT ATGCA
            11111 11111 11111 11111 11111 11111 11111 11111 11111 11111 11111 11111
XI12/8A     GACGA CCCAC TGTCT CTGCG CATGC TAGGT ATGCA TGGCA CGGTG TATGC AAATT ATGCA 1030        1040        1050        1060        1070        1080
XI12/8A     GTGGA TAAGG CCGAT CTGTT GCTTG CACTT GGTGT GCGGT TTGAT GATCG TGTGA CAGGG >
W22/1A      GTGGA TAAGG CCGAT CTGTT GCTTG CACTT GGTGT GCGGT TTGAT GATCG TGTGA CAGGG
            11111 11111 11111 11111 11111 11111 11111 11111 11111 11111 11111 11111
B73/7-4     GTGGA TAAGG CCGAT CTGTT GCTTG CACTT GGTGT GCGGT TTGAT GATCG cGTGA CAGGG >
            11111 11111 11111 11111 11111 11111 11111 11111 11111 11111 11111 11111
XI12/8A     GTGGA TAAGG CCGAT CTGTT GCTTG CACTT GGTGT GCGGT TTGAT GATCG TGTGA CAGGG
```

FIG. 7G

```
                   1090        1100        1110        1120        1130        1140
XI12/8A    AAGAT TGAGG CTTTT GCAAG CAGGG CTAAG ATTGT GCACG TTGAT ATTGA TCCGG CTGAG

W22/1A     AAGAT TGAGG CTTTT GCAAG CAGGG CTAAG ATTGT GCACG TTGAT ATTGA TCCGG CTGAG
           11111 11111 11111 11111 11111 11111 11111 11111 11111 11111 11111 11111
B73/7-4    AAGAT TGAGG CTTTT GCAAG CAGGG CTAAG ATTGT GCACG TTGAT ATTGA TCCGG CTGAG
           11111 11111 11111 11111 11111 11111 11111 11111 11111 11111 11111 11111
XI12/8A    AAGAT TGAGG CTTTT GCAAG CAGGG CTAAG ATTGT GCACG TTGAT ATTGA TCCGG CTGAG 1150        1160        1170        1180        1190        1200
XI12/8A    ATTGG CAAGA ACAAG CAGCC ACATG TGTCC ATCTG TGCAG ATGTT AAGCT TGCTT TGCAG

W22/1A     ATTGG CAAGA ACAAG CAGCC ACATG TGTCC ATCTG TGCAG ATGTT AAGCT TGCTT TGCAG
           11111 11111 11111 11111 11111 11111 11111 11111 11111 11111 11111 11111
B73/7-4    ATTGG CAAGA ACAAG CAGCC ACATG TGTCC ATCTG TGCAG ATGTT AAGCT TGCTT TGCAG
           11111 11111 11111 11111 11111 11111 11111 11111 11111 11111 11111 11111
XI12/8A    ATTGG CAAGA ACAAG CAGCC ACATG TGTCC ATCTG TGCAG ATGTT AAGCT TGCTT TGCAG 1210        1220        1230        1240        1250        1260
XI12/8A    GGCAT GAATG CTCTT CTTGA AGGAA GCACA TCAAA GAAGA GCTTT GACTT TGGCT CATGG

W22/1A     GGCAT GAATG CTCTT CTTGA AGGAA GCACA TCAAA GAAGA GCTTT GACTT TGGCT CATGG
           11111 11111 11111 11111 11111 11111 11111 11111 11111 11111 11111 11111
B73/7-4    GGCAT GAATG CTCTT CTTGA AGGAA GCACA TCAAA GAAGA GCTTT GACTT TGGCT CATGG
           11111 11111 11111 11111 11111 11111 11111 11111 11111 11111 11111 11111
XI12/8A    GGCAT GAATG CTCTT CTTGA AGGAA GCACA TCAAA GAAGA GCTTT GACTT TGGCT CATGG
```

FIG. 7H

```
                   1270        1280        1290        1300        1310        1320
XI12/8A   AACGA TGAGT TGGAT CAGCA GAAGA GGGAA TTCCC CCTTG GGTAT AAAAC ATCTA ATGAG
W22/1A    AACGA TGAGT TGGAT CAGCA GAAGA GGGAA TTCCC CCTTG GGTAT AAAAC ATCTA ATGAG
          11111 11111 11111 11111 11111 11111 11111 11111 11111 11111 11111 11111
B73/65    AACGA TGAGT TGGAT CAGCA GAAGA GGGAA TTCCC CCTTG GGTAT AAAAC ATCTA ATGAG
          11111 11111 11111 11111 11111 11111 11111 11111 11111 11111 11111 11111
XI12/8A   AACGA TGAGT TGGAT CAGCA GAAGA GGGAA TTCCC CCTTG GGTAT AAAAC ATCTA ATGAG 1330        1340        1350        1360        1370        1380
XI12/8A   GAGAT CCAGC CACAA TATGC TATTC AGGTT CTTGA TGAGC TGACG AAAGG CGAGG CCATC
W22/1A    GAGAT CCAGC CACAA TATGC TATTC AGGTT CTTGA TGAGC TGACG AAAGG CGAGG CCATC
          11111 11111 11111 11111 11111 11111 11111 11111 11111 11111 11111 11111
B73/7-4   GAGAT CCAGC CACAA TATGC TATTC AGGTT CTTGA TGAGC TGACG AAAGG CGAGG CCATC
          11111 11111 11111 11111 11111 11111 11111 11111 11111 11111 11111 11111
XI12/8A   GAGAT CCAGC CACAA TATGC TATTC AGGTT CTTGA TGAGC TGACG AAAGG CGAGG CCATC 1390        1400        1410        1420        1430        1440
XI12/8A   ATCGG CACAG GTGTT GGGCA GCACC AGATG TGGGC GGCAC AGTAC TACAC TTACA AGCGG
W22/1A    ATCGG CACAG GTGTT GGGCA GCACC AGATG TGGGC GGCAC AGTAC TACAC TTACA AGCGG
          11111 11111 11111 11111 11111 11111 11111 11111 11111 11111 11111 11111
B73/7-4   ATCGG CACAG GTGTT GGGCA GCACC AGATG TGGGC GGCAC AGTAC TACAC TTACA AGCGG
          11111 11111 11111 11111 11111 11111 11111 11111 11111 11111 11111 11111
XI12/8A   ATCGG CACAG GTGTT GGGCA GCACC AGATG TGGGC GGCAC AGTAC TACAC TTACA AGCGG
```

FIG. 7I

```
                1450        1460        1470        1480        1490        1500
XI12/8A         CCAAG GCAGT GGTTG TCTTC AGCTG GTCTT GGGGC TATGG GATTT GCCGG CTGCT
                      11111 11111 11111 11111 11111 11111 11111 11111 11111 11111
W22/1A          CCAAG GCAGT GGTTG TCTTC AGCTG GTCTT GGGGC TATGG GATTT GCCGG CTGCT
                      11111 11111 11111 11111 11111 11111 11111 11111 11111 11111
B73/7-4         CCAAG GCAGT GGTTG TCTTC AGCTG GTCTT GGGGC TATGG GATTT GCCGG CTGCT
                      11111 11111 11111 11111 11111 11111 11111 11111 11111 11111
XI12/8A         CCAAG GCAGT GGTTG TCTTC AGCTG GTCTT GGGGC TATGG GATTT GCCGG CTGCT 1510        1520        1530        1540        1550        1560
XI12/8A         GCTGG TGCTT CTGTG GCCAA CCCAG GTGTT ACTGT TGTTG ACATC GATGG AGATG GTAGC
                      11111 11111 11111 11111 11111         11111 11111 11111 11111 11111
W22/1A          GCTGG TGCTT CTGTG GCaAA CCCAG GTGTT ACTGT TGTTG ACATC GATGG AGATG GTAGC
                      11111 11111 11111 11111 11111   ^     11111 11111 11111 11111 11111
B73/7-4         GCTGG TGCTT CTGTG GCaAA CCCAG GTGTc ACTGT TGTTG ACATC GATGG AGATG GTAGC
                      11111 11111 11 11 11111 11111         11111 11111 11111 11111 11111
XI12/8A         GCTGG TGCTT CTGTG GCCAA CCCAG GTGTT ACTGT TGTTG ACATC GATGG AGATG GTAGC 1570        1580        1590        1600        1610        1620
XI12/8A         TTTCT CATGA ACGTT CAGGA GCTAG CTATG ATCCG AATTG AGAAC CTCCC GGTGA AGGTC
                      11111 11111 11111 11111 11111 11111 11111 11111 11111 11111 11111
W22/1A          TTTCT CATGA ACGTT CAGGA GCTAG CTATG ATCCG AATTG AGAAC CTCCC GGTGA AGGTC
                      11111 11111 11111 11111 11111 11111 11111 11111 11111 1111  11111
B73/7-4         TTTCT CATGA ACGTT CAGGA GCTAG CTATG ATCCG AATTG AGAAC CTCCC aGTGA AGGTC
                      11111 11111 11111 11111 11111 11111 11111 11111 11111   ^
                                                                              1111  11111
XI12/8A         TTTCT CATGA ACGTT CAGGA GCTAG CTATG ATCCG AATTG AGAAC CTCCC GGTGA AGGTC
```

FIG. 7J

```
                1630  1640  1650  1660  1670  1680
XI12/8A  TTTGT GCTAA ACAAC CAGCA CCTGG GGATG GTGGT GCAGT GGGAG GACAG GTTCT ATAAG
W22/1A   TTTGT GCTAA ACAAC CAGCA CCTGG GGATG GTGGT GCAGT GGGAG GACAG GTTCT ATAAG
         11111 11111 11111 11111 11111 11111 11111 11111  #
B73/7-4  TTTGT GCTAA ACAAC CAGCA CCTGG GGATG GTGGT GCAGT tGGAG GACAG GTTCT ATAAG
         11111 11111 11111 11111 11111 11111 11111 11111 1111  11111 11111 11111
XI12/8A  TTTGT GCTAA ACAAC CAGCA CCTGG GGATG GTGGT GCAGT GGGAG GACAG GTTCT ATAAG 1690  1700  1710  1720  1730  1740
XI12/8A  GCCAA CAGAG CGCAC ACATA CTTGG GAAAC CCAGA GAATG AAAGT GAGAT ATATC CAGAT
W22/1A   GCCAG CAGAG CGCAC ACATA CTTGG GAAAC CCAGA GAATG AAAGT GAGAT ATATC CAGAT
         11111 11111 11111 11111 11111 11111 11111 11111 11111 11111 11111 11111
B73/7-4  GCCAG CAGAG CGCAC ACATA CTTGG GAAAC CCAGA GAATG AAAGT GAGAT ATATC CAGAT
         11111 11111 11111 11111 11111 11111 11111 11111 11111 11111 11111 11111
XI12/8A  GCCAG CAGAG CGCAC ACATA CTTGG GAAAC CCAGA GAATG AAAGT GAGAT ATATC CAGAT 1750  1760  1770  1780  1790  1800
XI12/8A  TTCGT GACGA TCGCC AAAGG GTTCA ACATT CCAGC GGTCC GTGTG ACAAA GAAGA ACGAA
W22/1A   TTCGT GACGA TCGCC AAAGG GTTCA GTTCA ACATT CCAGC GGTCC GTGTG ACAAA GAAGA ACGAA
         11111 11111 11111 11111 11111 11111 11111 11111 11111 11111 11111 11111
B73/7-4  TTCGT GACGA TCGCC AAAGG GTTCA ACATT CCAGC GGTCC GTGTG ACAAA GAAGA ACGAA
         11111 11111 11111 11111 11111 11111 11111 11111 11111 11111 11111 11111
XI12/8A  TTCGT GACGA TCGCC AAAGG GTTCA ACATT CCAGC GGTCC GTGTG ACAAA GAAGA ACGAA
```

FIG. 7K

```
                 1810        1820        1830        1840        1850        1860
XI12/8A    GTCCG CGCAG CGATA AAGAA GATGC TCGAG ACTCC AGGGC CGTAC CTCTT GGATA TAATC
W22/1A     GTCCG CGCAG CGATA AAGAA GATGC TCGAG ACTCC AGGGC CGTAC CTCTT GGATA TAATC
           11111 11111 11111 11111 11111 11111 11111 11111 11111 11111 11111 11111
B73/7-4    GTCCG CGCAG CGATA AAGAA GATGC TCGAG ACTCC AGGGC CGTAC CTCTT GGATA TAATC
           11111 11111 11111 11111 11111 11111 11111 11111 11111 11111 11111 11111
XI12/8A    GTCCG CGCAG CGATA AAGAA GATGC TCGAG ACTCC AGGGC CGTAC CTCTT GGATA TAATC 1870        1880        1890        1900        1910        1920
                                                      *
XI12/8A    GTCCC ACACC AGGAG CATGT GTTGC CTATG ATCCC TAATG GTGGG GCTTT CAAGG ATATG
W22/1A     GTCCC ACACC AGGAG CATGT GTTGC CTATG ATCCC TAgTG GTGGG GCTTT CAAGG ATATG
           11111 11111 11111 11111 11111 11111 11111 11 11 11111 11111 11111 11111
B73/7-4    GTCCC ACACC AGGAG CATGT GTTGC CTATG ATCCC TAgTG GTGGG GCTTT CAAGG ATATG
           11111 11111 11111 11111 11111 11111 11111 11111 11111 11111 11111 11111
XI12/8A    GTCCC ACACC AGGAG CATGT GTTGC CTATG ATCCC TAATG GTGGG GCTTT CAAGG ATATG 1930        1940        1950        1960
XI12/8A    ATCCT GGATG GTGAT GGCAG GACTG TGTAC TGATC TAAAA TCCAG CAAG
W22/1A     ATCCT GGATG GTGAT GGCAG GACTG TGTAC TGATC TAAAA TCCAG CAAG>
           11111 11111 11111 11111 11111 11111 11111 11111 11111 1111
B73/7-4    ATCCT GGATG GTGAT GGCAG GACTG TGTAC TGATC TAAAA TCCAG CAAG>
           11111 11111 11111 11111 11111 11111 11111 11111 11111 1111
XI12/8A    ATCCT GGATG GTGAT GGCAG GACTG TGTAC TGATC TAAAA TCCAG CAAG
```

FIG. 8A

```
                    10           20           30           40           50           60
XI12/8A    MATAA AASTA LTGAT TAAPK ARRRA HLLAT RRALA APIRC SAASP AMPMA PPATP LRPWG
W22/1A     MATAA AASTA LTGAT TAAPK ARRRA HLLAT RRALA APIRC SAASP AMPMA PPATP LRPWG
           11111 11111 121 1 11111 11111 11111 11111 11111 11111 11111 11111 11111
B73/7-4    MATAA AASTA LTGAT TAAPK ARRRA HLLAT RRALA APIRC SAASP AMPMA PPATP LRPWG
           11111 11111 11111 11111 11111 11111 11111 11111 11111 11111 11111 11111
XI12/8A    MATAA AASTA LTGAT TAAPK ARRRA HLLAT RRALA APIRC SAASP AMPMA PPATP LRPWG 70           80           90          100          110          120
XI12/8A    PTDPR KGADI LVESL ERCGV RDVFA YPGGA SMEIH QALTR SPVIA NHLFR HEQGE AFAAS
W22/1A     PTDPR KGADI LVESL ERCGV RDVFA YPGGA SMEIH QALTR SPVIA NHLFR HEQGE AFAAS
           11 11 11111 11111 11111 11111 11111 11111 11111 11111 11111 11111 11111
B73/7-4    PTePR KGADI LVESL ERCGV RDVFA YPGGA SMEIH QALTR SPVIA NHLFR HEQGE AFAAS
           11 11 11111 11111 11111 11111 11111 11111 11111 11111 11111 11111 11111
XI12/8A    PTDPR KGADI LVESL ERCGV RDVFA YPGGA SMEIH QALTR SPVIA NHLFR HEQGE AFAAS 130          140          150          160          170          180
XI12/8A    GYARS SGRVG VCIAT SGPGA TNLVS ALADA LLDSV PMVAI TGQVP RRMIG TDAFQ ETPIV
W22/1A     GYARS SGRVG VCIAT SGPGA TNLVS ALADA LLDSV PMVAI TGQVP RRMIG TDAFQ ETPIV
           11111 11111 11111 11111 11111 11111 11111 11111 11111 11111 11111 11111
B73/7-4    GYARS SGRVG VCIAT SGPGA TNLVS ALADA LLDSV PMVAI TGQVP RRMIG TDAFQ ETPIV
           11111 11111 11111 11111 11111 11111 11111 11111 11111 11111 11111 11111
XI12/8A    GYARS SGRVG VCIAT SGPGA TNLVS ALADA LLDSV PMVAI TGQVP RRMIG TDAFQ ETPIV
```

FIG. 8B

```
              190         200         210         220         230         240
XI12/8A    EVTRS ITKHN YLVLD VDDIP RVVQE AFFLA SSGRP GPVLV DIPKD IQQQM AVPVW DKPMS
W22/1A     EVTRS ITKHN YLVLD VDDIP RVVQE AFFLA SSGRP GPVLV DIPKD IQQQM AVPVW DKPMS
           11111 11111 11111 11111 11111 11111 11111 11111 11111 11111 11111 11111
B73/7-4    EVTRS ITKHN YLVLD VDDIP RVVQE AFFLA SSGRP GPVLV DIPKD IQQQM AVPVW DKPMS
           11111 11111 11111 11111 11111 11111 11111 11111 11111 11111 11111 11111
XI12/8A    EVTRS ITKHN YLVLD VDDIP RVVQE AFFLA SSGRP GPVLV DIPKD IQQQM AVPVW DKPMS 250         260         270         280         290         300
XI12/8A    LPGYI ARLPK PPATE LLEQV LRLVG ESRRP VLYVG GGCAA SGEEL RRFVE LTGIP VTTTL
W22/1A     LPGYI ARLPK PPATE LLEQV LRLVG ESRRP VLYVG GGCAA SGEEL RRFVE LTGIP VTTTL
           11111 11111 11111 11111 11111 11111 11111 11111 11111 11111 11111 11111
B73/7-4    LPGYI ARLPK PPATE LLEQV LRLVG ESRRP VLYVG GGCAA SGEEL RRFVE LTGIP VTTTL
           11111 11111 11111 11111 11111 11111 11111 11111 11111 11111 11111 11111
XI12/8A    LPGYI ARLPK PPATE LLEQV LRLVG ESRRP VLYVG GGCAA SGEEL RRFVE LTGIP VTTTL 310         320         330         340         350         360
XI12/8A    MGLGN FPSDD PLSLR MLGMH GTVYA NYAVD KADLL LALGV RFDDR VTGKI EAFAS RAKIV
W22/1A     MGLGN FPSDD PLSLR MLGMH GTVYA NYAVD KADLL LALGV RFDDR VTGKI EAFAS RAKIV
           11111 11111 11111 11111 11111 11111 11111 11111 11111 11111 11111 11111
B73/7-4    MGLGN FPSDD PLSLR MLGMH GTVYA NYAVD KADLL LALGV RFDDR VTGKI EAFAS RAKIV
           11111 11111 11111 11111 11111 11111 11111 11111 11111 11111 11111 11111
XI12/8A    MGLGN FPSDD PLSLR MLGMH GTVYA NYAVD KADLL LALGV RFDDR VTGKI EAFAS RAKIV
```

FIG. 8C

```
                370         380         390         400         410         420
XI12/8A    HVDID PAEIG KNKQP HVSIC ADVKL ALQGM NALLE GSTSK KSFDF GSWND ELDQQ KREFP

W22/1A     HVDID PAEIG KNKQP HVSIC ADVKL ALQGM NALLE GSTSK KSFDF GSWND ELDQQ KREFP
           11111 11111 11111 11111 11111 11111 11111 11111 11111 11111 11111 11111
B73/7-4    HVDID PAEIG KNKQP HVSIC ADVKL ALQGM NALLE GSTSK KSFDF GSWND ELDQQ KREFP
           11111 11111 11111 11111 11111 11111 11111 11111 11111 11111 11111 11111
XI12/8A    HVDID PAEIG KNKQP HVSIC ADVKL ALQGM NALLE GSTSK KSFDF GSWND ELDQQ KREFP 430         440         450         460         470         480
XI12/8A    LGYKT SNEEI QPQYA IQVLD ELTKG EAIIG TGVGQ HQMWA AQYYT YKRPR QWLSS AGLGA

W22/1A     LGYKT SNEEI QPQYA IQVLD ELTKG EAIIG TGVGQ HQMWA AQYYT YKRPR QWLSS AGLGA
           11111 11111 11111 11111 11111 11111 11111 11111 11111 11111 11111 11111
B73/7-4    LGYKT SNEEI QPQYA IQVLD ELTKG EAIIG TGVGQ HQMWA AQYYT YKRPR QWLSS AGLGA
           11111 11111 11111 11111 11111 11111 11111 11111 11111 11111 11111 11111
XI12/8A    LGYKT SNEEI QPQYA IQVLD ELTKG EAIIG TGVGQ HQMWA AQYYT YKRPR QWLSS AGLGA 490         500         510         520         530         540
XI12/8A    MGFGL PAAAG ASVAN PGVTV VDIDG DGSFL MNVQE LAMIR IENLP VKVFV LNNQH LGMVV

W22/1A     MGFGL PAAAG ASVAN PGVTV VDIDG DGSFL MNVQE LAMIR IENLP VKVFV LNNQH LGMVV
           11111 11111 11111 11111 11111 11111 11111 11111 11111 11111 11111 11111
B73/7-4    MGFGL PAAAG ASVAN PGVTV VDIDG DGSFL MNVQE LAMIR IENLP VKVFV LNNQH LGMVV
           11111 11111 11111 11111 11111 11111 11111 11111 11111 11111 11111 11111
XI12/8A    MGFGL PAAAG ASVAN PGVTV VDIDG DGSFL MNVQE LAMIR IENLP VKVFV LNNQH LGMVV
```

FIG. 8D

```
                550         560         570         580         590         600
XI12/8A  QWEDR FYKAN RAHTY LGNPE NESEI YPDFV TIAKG FNIPA VRVTK KNEVR AAIKK MLETP
W22/1A   QWEDR FYKAN RAHTY LGNPE NESEI YPDFV TIAKG FNIPA VRVTK KNEVR AAIKK MLETP
         1 111 11111 11111 11111 11111 11111 11111 11111 11111 11111 11111 11111
              *
B73/7-4  QlEDR FYKAN RAHTY LGNPE NESEI YPDFV TIAKG FNIPA VRVTK KNEVR AAIKK MLETP
         1 111 11111 11111 11111 11111 11111 11111 11111 11111 11111 11111 11111
XI12/8A  QWEDR FYKAN RAHTY LGNPE NESEI YPDFV TIAKG FNIPA VRVTK KNEVR AAIKK MLETP 610         620         630
XI12/8A  GPYLL DIIVP HQEHV LPMIP NGGAF KDMIL DGDGR TVY*
W22/1A   GPYLL DIIVP HQEHV LPMIP sGGAF KDMIL DGDGR TVY>
         11111 11111 11111 11111 11111 11111 11111 111
                                 *
B73/7-4  GPYLL DIIVP HQEHV LPMIP sGGAF KDMIL DGDGR TVY>
         11111 11111 11111 11111  1111 11111 11111 111
XI12/8A  GPYLL DIIVP HQEHV LPMIP NGGAF KDMIL DGDGR TVY
```

IMIDAZOLINONE RESISTANT AHAS MUTANTS

This invention relates to novel DNA sequences that encode novel variant forms of acetohydroxy acid synthase enzyme (hereinafter AHAS). The AHAS enzyme is a critical enzyme routinely produced in a variety of plants and a broad range of microorganisms. Normal AHAS function is inhibited by imidazolinone herbicides; however, new AHAS enzymes encoded by the mutant DNA sequences function normally catalytically even in the presence of imidazolinone herbicides and, therefore, confer herbicide resistance upon the plant or microorganism containing them.

The novel DNA sequences are derived from corn and have a substitution of an amino acid at position 621 of the normal AHAS sequence. This substitution in the AHAS gene sequence results in a fully functional enzyme, but renders the enzyme specifically resistant to inhibition by a variety of imidazolinone herbicides. The availability of these variant sequences provides a tool for transformation of different crop plants to imidazolinone herbicide resistance, as well as providing novel selectable markers for use in other types of genetic transformation experiments.

BACKGROUND OF THE INVENTION

The use of herbicides in agriculture is now widespread. Although there are a large number of available compounds which effectively destroy weeds, not all herbicides are capable of selectively targeting the undersirable plants over crop plants, as well as being non-toxic to animals. Often, it is necessary to settle for compounds which are simply less toxic to crop plants than to weeds. In order to overcome this problem, development of herbicide resistant crop plants has become a major focus of agricultural research.

An important aspect of development of herbicide-resistance is an understanding of the herbicide target, and then manipulating the affected biochemical pathway in the crop plant so that the inhibitory effect is avoided while the plant retains normal biological function. One of the first discoveries of the biochemical mechanism of herbicides related to a series of structurally unrelated herbicide compounds, the imidazolinones, the sulfonylureas and the triazolopyrimidines. It is now known (Shaner et al. *Plant Physiol.* 76: 545–546,1984; U.S. Pat. No. 4,761,373) that each of these herbicides inhibits plant growth by interference with an essential enzyme required for plant growth, acetohydroxyacid synthase (AHAS; also referred to as acetolacetate synthase, or ALS). AHAS is required for the synthesis of the amino acids isoleucine, leucine and valine.

The AHAS enzyme is known to be present throughout higher plants, as well as being found in a variety of microorganisms, such as the yeast *Saccharomyces cerevisiae*, and the enteric bacteria, *Escherichia coli* and *Salmonella typhimurium*. The genetic basis for the production of normal AHAS in a number of these species has also been well characterized. For example, in both *E. coli* and *S. typhimurium* three isozymes of AHAS exist; two of these are sensitive to herbicides while a third is not. Each of these isozymes possesses one large and one small protein subunit; and map to the IlvIH, IlvGM and IlvBN operons. In yeast, the single AHAS isozyme has been mapped to the ILV2 locus. In each case, sensitive and resistant forms have been identified and sequences of the various alleles have been determined (Friden et. al., *Nucl. Acid Res.* 13: 3979–3998, 1985; Lawther et al., *PNAS USA* 78: 922–928, 1982; Squires et al., *Nucl. Acids Res* 811: 5299–5313, 1983; Wek et al; *Nucl. Acids Res* 13: 4011–4027, 1985; Falco and Dumas, *Genetics* 109, 21–35, 985; Falco et al, *Nucl. Acids Res* 13; 4011–4027, 1985).

In tobacco, AHAS function is encoded by two unlinked genes, SuRA and SuRB. There is substantial identity between the two genes, both at the nucleotide level and amino acid level in the mature protein, although the N-terminal, putative transit region differs more substantially (Lee et al, *EMBO J.* 7: 1241–1248, 1988). Arabidopsis, on the other hand, has a single AHAS gene, which has also been completely sequenced (Mazur et al., *Plant Physiol.* 85:1110–1117, 1987). Comparisons among sequences of the AHAS genes in higher plants indicates a high level of conservation of certain regions of the sequence; specifically, there are at least 10 regions of sequence conservation. It has previously been assumed that these conserved regions are critical to the function of the enzyme, and that retention of that function is dependent upon substantial sequence conservation.

It has been recently reported (U.S. Pat. No. 5,013,659) that mutants exhibiting herbicide resistance possess mutations in at least one amino acid in one or more of these conserved regions. In particular, substitution of certain amino acids for the wild type amino acid at these specific sites in the AHAS protein sequence have been shown to be tolerated, and indeed result in herbicide resistance of the plant possessing this mutation, while retaining catalytic function. The mutations described therein encode either cross resistance for imidazolinones and sulfonylureas or sulfonylurea-specific resistance, but no imidazolinone-specific mutations were disclosed. These mutations have been shown to occur at both the SuRA and SuRB loci in tobacco; similar mutations have been isolated in Arabidopsis and yeast.

Imidazolinone-specific resistance has been reported elsewhere in a number of plants. U.S. Pat. No. 4,761,373 generally described an altered AHAS as a basis of herbicide resistance in plants, and specifically disclosed certain imidazolinone resistant corn lines. Haughn et al. (*Mol. Gen. Genet.* 211:266–271, 1988) disclosed the occurrence of a similar phenotype in Arabidopsis. Sathasivan et al. (Nucl. Acid Res. 18:2188, 1990) identified the imidazolinone-specific resistance in Arabidopsis as being based on a mutation at position 653 in the normal AHAS sequence. In accordance with the present invention, a gene encoding imidazolinone-specific resistance in a monocot has now been isolated and determined to be associated with a single amino acid substitution in a wild-type monocot AHAS amino acid sequence.

SUMMARY OF THE INVENTION

The present invention provides novel nucleic acid sequences encoding functional monocot AHAS enzymes insensitive to imidazolinone herbicides. The sequences in question comprise a mutation in the codon encoding the amino acid serine at position 621 in the corn (maize) AHAS sequence, or in the corresponding position in other monocot sequences. Other monocots, such as wheat, are also known to exhibit imidazolinone specific mutations (e.g., ATCC Nos. 40994–97). In corn, the wild type sequence has a serine at this position. In a preferred embodiment, the substitution is asparagine for serine, but alternate substitutions for serine include aspartic acid, glutamic acid, glutamine and tryptophane. Although the claimed sequences are originally derived from monocots, the novel sequences are useful in methods for producing imidazolinone resistant cells in any type of plant, said methods comprising transforming a target plant cell with one or more of the altered sequences provided herein. Alternatively, mutagenesis is utilized to create mutants in plant cells or seeds containing a nucleic acid sequence encoding an imidazolinone insensitive AHAS. In the case of mutant plant cells isolated in tissue culture, plants which possess the imidazolinone resistant or insensitive trait are then regenerated. The invention thus also encompasses plant cells, bacterial cells, fungal cells, plant tissue cultures, adult plants, and plant seeds that possess a mutant nucleic acid sequence and which express functional imidazolinone resistant AHAS enzymes.

The availability of these novel herbicide resistant plants enables new methods of growing crop plants in the presence of imidazolinones. Instead of growing non-resistant plants, fields may be planted with the resistant plants produced by mutation or by transformation with the mutant sequences of the present invention, and the field routinely treated with imidazolinones, with no resulting damage to crop plants.

The mutant nucleic acids of the present invention also provide novel selectable markers for use in transformation experiments. The nucleic acid sequence encoding a resistant AHAS is linked to a second gene prior to transfer to a host cell, and the entire construct transformed into the host. Putative transformed cells are then grown in culture in the presence of inhibitory amounts of herbicide; surviving cells will have a high probability of having successfully acquired the second gene of interest. Alternately, the resistant AHAS gene can be cotransformed on an independent plasmid with the gene of interest, whereby about 50% of all transformants can be expected to have received both genes.

The following definitions should be understood to apply throughout the specification and claims. A "functional" or "normal" AHAS enzyme is one which is capable of catalyzing the first step in the pathway for synthesis of the essential amino acids isoleucine, leucine and valine. A "wild-type" AHAS sequence is a sequence present in an imidazolinone sensitive member of a given species. A "resistant" plant is one which produces a mutant but functional AHAS enzyme, and which is capable of reaching maturity when grown in the presence of normally inhibitory levels of imidazolinone. The term "resistant", as used herein, is also intended to encompass "tolerant" plants, i.e., those plants which phenotypically evidence adverse, but not lethal, reactions to the imidazolinone.

BRIEF DESCRIPTION OF THE FIGURES

FIGS. (1A and B): AHAS enzyme activity in 10-day old maize seedlings (corn lines A619 or XI12) in the presence of imazethapyr (Pursuit™, A) or sulfometuron methyl (Oust™, B). Herbicide resistant AHAS activity is calculated as percentage of AHAS activity in the absence of inhibitor.

FIGS. 6A–6I: Nucleotide and deduced amino acid sequences of the XI12/8A mutant AHAS gene.

FIGS. 7A–7K: Nucleotide sequence alignment of XI12/8A, B73/7-4 and W22/1A als2 genes. (*) marks the base change causing the mutation at position 621, (#) differences from the B73/7-4 sequence and (>) represents silent changes.

FIGS. 8A–8D: Amino acid sequences and alignment of XI12/BA, B73/7-4 and W22/1A als2 genes. (*) marks the mutation at position 621, (#) marks differences from the B73/7-4 sequence, and (>) represents silent changes.

DETAILED DESCRIPTION OF THE INVENTION

The gene of the present invention is isolatable from corn maize line XI12 (seed deposited with the American Type Culture Collection as Accession Number 75051), and has been inserted into plasmid pXI12/8A (deposited with the American Type Culture Collection as Accession Number 68643). It is also isolatable from any other imidazolinone-specific herbicide resistant mutant, such as the corn line QJ22 (deposited as a cell culture with the American Type Culture Collection as Accession Number 40129), or the various wheat plants (seed deposited with the American Type Collection as Accession Numbers 40994, 40995, 40996, or 40997). A genomic DNA library is created, for example, in phage EMBL-3 with DNA from one of the imidazolinone resistant mutants, preferably one which is homozygous for the resistance trait, and is screened with a nucleic acid probe comprising all or a part of a wild-type AHAS sequence.

In maize, the AHAS gene is found at two loci, als1 and als2 (Burr and Burr, Trends in Genetics 7:55–61, 1991); the homology between the two loci is 95% at the nucleotide level. The mutation in XI12 is mapped to locus als2 on chromosome 5, whereas the nonmutant gene is mapped to locus als1 on chromosome 4 (Newhouse et al., "Imidazolinone-resistant crops". In The Imidazolinone Herbicides, Shaner and O'Connor (Eds.), CRC Press, Boca Raton, Fla., in Press) Southern analysis identifies some clones containing the mutant als2 gene, and some containing the non-mutant als1 gene. Both types are subcloned into sequencing vectors, and sequenced by the dideoxy sequencing method.

Figures 4, 5B:
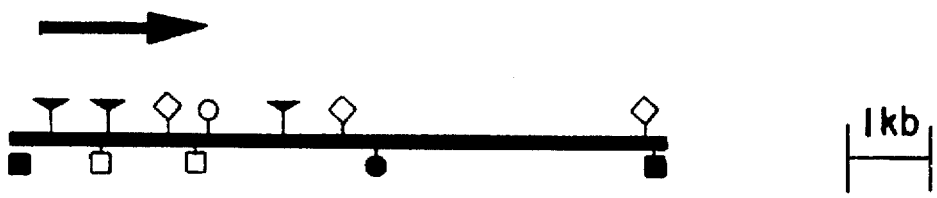
FIG. 4: Restriction map of plasmid pCD8A. The mutant AHAS gene from XI12 was subcloned as a 8 kb PstI fragment into vector pKS(+). The location and orientation of the AHAS gene is indicated by an arrow. The restriction sites of PstI, XhoI, HindIII, XbaI and ClaI are represented by symbols.
Figure 5A:
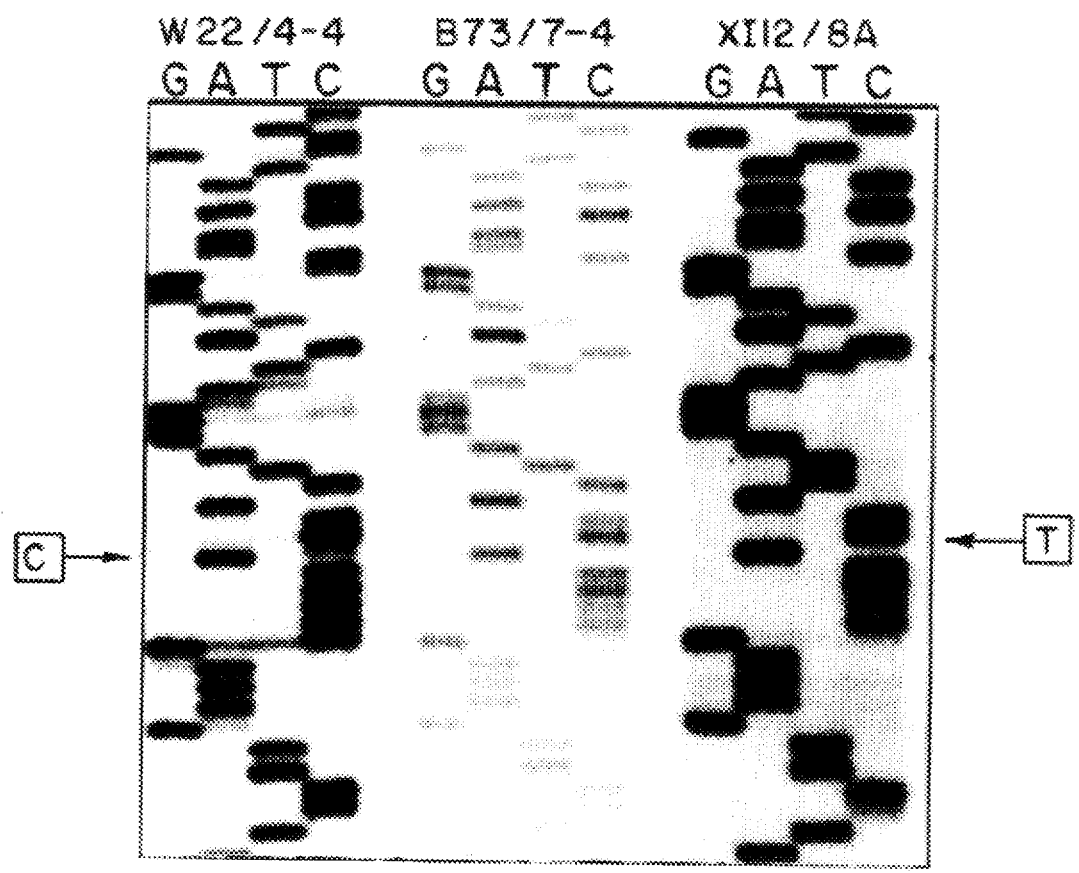
FIGS. 5(A and 5B): Nucleotide sequencing gel of the non-coding strand (A) and the double stranded DNA sequence (B) of AHAS clones W22/4-4, B73/10-4 and XI12/8A in the region of amino acids 614 to 633. The position of the cytosine to thymidine transition is indicated by an arrow.

Sequencing and comparison of wild type and mutant AHAS genes shows a difference of a single nucleotide in the codon encoding the amino acid at position 621 (FIG. 5). Specifically, the codon AGT encoding serine in the wild type is changed to AAT encoding asparagine in the mutant AHAS (FIG. 8). The mutant AHAS gene is otherwise similar to the wild type gene, encoding a protein having 638 amino acids, the first 40 of which constitute a transit peptide which is thought to be cleaved during transport into the chloroplast in vivo. The sequence of the als1 non-mutant gene from XI12 appears to be identical to the als1 gene from B73.

The mutant genes of the present invention confer resistance to imidazolinone herbicides, but not to sulfonylurea herbicides. Types of herbicides to which resistance is conferred are described for example in U.S Pat. Nos. 4,188,487; 4,201,565; 4,221,586; 4,297,128; 4,554,013; 4,608,079; 4,638,068; 4,747,301; 4,650,514; 4,698,092; 4,701,208; 4,709,036; 4,752,323; 4,772,311; and 4,798,619.

It will be understood by those skilled in the art that the nucleic acid sequence depicted in FIG. 6 is not the only sequence which can be used to confer imidazolinone-specific resistance. Also contemplated are those nucleic acid sequences which encode an identical protein but which, because of the degeneracy of the genetic code, possess a different nucleotide sequence. The invention also encompasses genes encoding AHAS sequences in which the aforestated mutation is present, but which also encode one or more silent amino acid changes in portions of the molecule not involved with resistance or catalytic function. Also contemplated are gene sequences from other imidazolinone resistant monocots which have a mutation in the corresponding region of the sequences.

For example, alterations in the gene sequence which result in the production of a chemically equivalent amino acid at a given site are contemplated; thus, a codon for the amino acid alanine, a hydrophobic amino acid, can readily be substituted by a codon encoding another hydrophobic residue, such as glycine, or may be substituted with a more hydrophobic residue such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. The invention also encompasses chimaeric genes, in which the substituted portion of the corn AHAS gene is recombined with unaltered portions of the normal AHAS genes from other species. Thus, throughout the specification and claims, wherever the term "imidazolinone-specific resistant corn AHAS gene" is used, it is intended to cover each of these alternate embodiments as well as the sequence of FIG. 6.

Isolated AHAS DNA sequences of the present invention are useful to transform target crop plants, and thereby confer imidazolinone resistance. A broad range of techniques currently exist for achieving direct or indirect transformation of higher plants with exogenous DNA, and any method by which the novel sequence can be incorporated into the host genome, and stably inherited by its progeny, is contemplated by the present invention. The imidazolinone specific resistance trait is inherited as a single dominant nuclear gene. The level of imidazolinone resistance is increased when the gene is present in a homozygous state; such corn plants, for example, have a resistance level of about 1,000 times that of a non-resistant plant. Plants heterozygous for the trait, however, have a resistance of about 50–500 times that of a non-resistant plant.

Transformation of plant cells can be mediated by the use of vectors. A common method of achieving transformation is the use of *Agrobacterium tumefaciens* to introduce a foreign gene into the target plant cell. For example, the mutant AHAS sequence is inserted into a plasmid vector containing the flanking sequences in the Ti-plasmid T-DNA. The plasmid is then transformed into *E. coli*. A triparental mating among this strain, an Agrobacterium strain containing a disarmed Ti-plasmid containing the virulence functions needed to effect transfer of the AHAS containing T-DNA sequences into the target plant chromosome, and a second *E. coli* strain containing a plasmid having sequences necessary to mobilize transfer of the AHAS construct from *E. coli* to Agrobacterium is carried out. A recombinant Agrobacterium strain, containing the necessary sequences for plant transformation is used to infect leaf discs. Discs are grown on selection media and successfully transformed regenerants are identified. The recovered plants are resistant to the effects of herbicide when grown in its presence. Plant viruses also provide a possible means for transfer of exogenous DNA.

Direct uptake of plant cells can also be employed. Typically, protoplasts of the target plant are placed in culture in the presence of the DNA to be transferred, and an agent which promotes the uptake of DNA by protoplast. Useful agents in this regard are polyethylene glycol or calcium phosphate.

Alternatively, DNA uptake can be stimulated by electroporation. In this method, an electrical pulse is used to open temporary pores in a protoplast cell membrane, and DNA in the surrounding solution is then drawn into the cell through the pores. Similarly, microinjection can be employed to deliver the DNA directly into a cell, and preferably directly into the nucleus of the cell.

In each of the foregoing techniques, transformation occurs in a plant cell in culture. Subsequent to the transformation event, plant cells must be regenerated to whole plants. Techniques for the regeneration of mature plants from callus or protoplast culture are now well known for a large number of different species (see, e.g., *Handbook of Plant Cell Culture*, Vols. 1–5, 1983–1989 McMillan, N.Y.) Thus, once transformation has been achieved, it is within the knowledge in the art to regenerate mature plants from the transformed plant cells.

Alternate methods are also now available which do not necessarily require the use of isolated cells, and therefore, plant regeneration techniques, to achieve transformation. These are generally referred to as "ballistic" or "particle acceleration" methods, in which DNA coated metal particles are propelled into plant cells by either a gunpowder charge (Klein et al., *Nature* 327: 70–73, 1987) Or electrical discharge (EPO 270 356). In this manner, plant cells in culture or plant reproductive organs or cells, e.g. pollen, can be stably transformed with the DNA sequence of interest.

In certain dicots and monocots direct uptake of DNA is the preferred method of transformation. For example, in corn, the cell wall of cultured cells is digested in a buffer with one or more cell wall degrading enzymes, such as cellulase, hemicellulase and pectinase, to isolate viable protoplasts. The protoplasts are washed several times to remove the enzymes, and mixed with a plasmid vector containing the gene of interest. The cells can be transformed with either PEG (e.g. 20% PEG 4000) or by electroporation. The protoplasts are placed on a nitrocellulose filter and cultured on a medium with embedded corn cells functioning as feeder cultures. After 2–4 weeks, the cultures in the nitrocellulose filter are placed on a medium containing about 0.32 μM of the imidazolinone and maintained in the medium for 1–2 months. The nitrocellulose filters with the plant cells are transferred to fresh medium with herbicides and nurse cells every two weeks. The untransformed cells cease growing and die after a few weeks.

The present invention can be applied to transformation of virtually any type of plant, both monocot and dicot. Among the crop plants for which transformation to herbicide resistance is contemplated are corn, wheat, rice, millet, oat, barley, sorghum, sunflower, sweet potato, alfalfa, sugar beet, Brassica species, tomato, pepper, soybean, tobacco, melon, squash, potato, peanut, pea, cotton, or cacao. The novel sequences may also be used to transform ornamental species, such as rose, and woody species, such as pine and poplar.

The novel sequences of the invention also are useful as selectable markers in plant genetics studies. For example, in plant transformation, sequences encoding imidazolinone resistance could be linked to a gene of interest which is to be used to transform a target imidazolinone sensitive plant cell. The construct comprising both the gene of interest and the imidazolinone resistant sequence are introduced into the plant cell, and the plant cells are then grown in the presence of an inhibitory amount of an imidazolinone. Alternately, the second gene of interest can be cotransformed, on a separate plasmid, into the host cells. Plant cells surviving such treatment presumably have acquired the resistance gene as well as the gene of interest, and therefore, only transformants survive the selection process with the herbicide. Confirmation of successful transformation and expression of both genes can be achieved by Southern hybridization of genomic DNA, by PCR or by observation of the phenotypic expression of the genes.

The invention is further illustrated by the following non-limiting examples.

EXAMPLES

1. Confirmation of Whole Plant Herbicide Resistance in XI12

XI12 plants are treated with herbicides at 10 days to the V3 leaf stage (4–5 leaves, of which 3 have visible ligules). Imazethapyr is applied at rates of 2000, 500, 250, 125 and 62.5 g/ha. Chlorsulfuron is applied at 32, 16, 8, 4 and 2 g/ha. Plants are treated postemergence at a spray volume of 400 l/ha. After spraying, plants are placed in the greenhouse for further observation.

XI12 plants are unaffected at all rates of imazethapyr treatment; however, no visible increased resistance to chlorsulfuron is noted. Thus, XI12 displays selective resistance to the imidazolinone at the whole plant level (See FIG. 1).

The resistance in XI12 is also shown to be inherited as a single dominant allele of a nuclear gene. Heterozygous resistant XI12 are selfed, and the selfed progeny segregate in the 3 resistant:1 susceptible ratio expected for a single dominant allele of a nuclear gene. In this study, the segregating seedlings are sprayed postemergence with lethal doses of imazethapyr (125 or 250 g/ha) following spraying protocols described above, to establish segregation for resistance.

2. AHAS Extraction

Seeds of XI12 are sown in soil in a greenhouse maintained at day/night temperature of 80° C. and 15 hour photoperiod. Plants are harvested two weeks after planting. The basal portion of the shoot is used for the extraction of AHAS. 5 g of the tissue is powdered in liquid nitrogen and then homogenized in AHAS assay buffer comprising 100 mM potassium phosphate buffer (pH 7.5) containing 10 mH pyruvate, 5 mM $MgCl_2$, 5 mM EDTA, 100 uM FAD (flavin adenine dinucleotide), 1 mM valine, 1 mM leucine, 10% glycerol and 10 mM cysteine. The homogenate is centrifuged at 10,000 rpm for 10 minutes and 3 ml of the supernatant are applied onto an equilibrated Bio-Rad Econo-Desalting column (10 DG) and eluted with 4 ml AHAS assay buffer.

AHAS activity is measured by estimation of the product, acetolactate, after conversion by decarboxylation in the presence of acid to acetoin. Standard reaction mixtures contain the enzyme in 50 mM potassium phosphate (pH 7.0) containing 100 mM sodium pyruvate, 10 mM $MgCl_2$, 1 mM thiamine pyrophosphate, 10 uM FAD, and appropriate concentrations of different inhibitors. This mixture is incubated at 37° C. for 1 to 3 hours depending upon the experiment. At the end of this incubation period, the reaction is stopped with the addition of $H_2SO_4$ to make a final concentration of 0.85% $H_2SO_4$ in the tube. The reaction product is allowed to decarboxylate at 60° C. for 15 minutes. The acetoin formed is determined by incubating with creatine (0.17%) and 1-naphthol (1.7% in 4N NaOH). The absorption of color complex formed is measured at 520 nm.

Figure 1A:
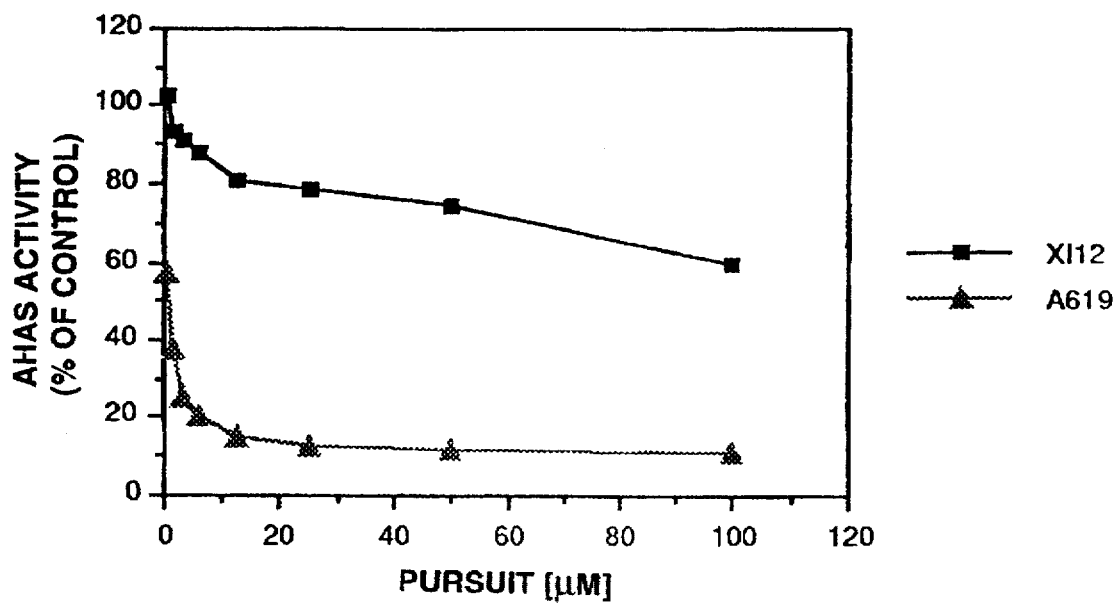
Figure 1B:
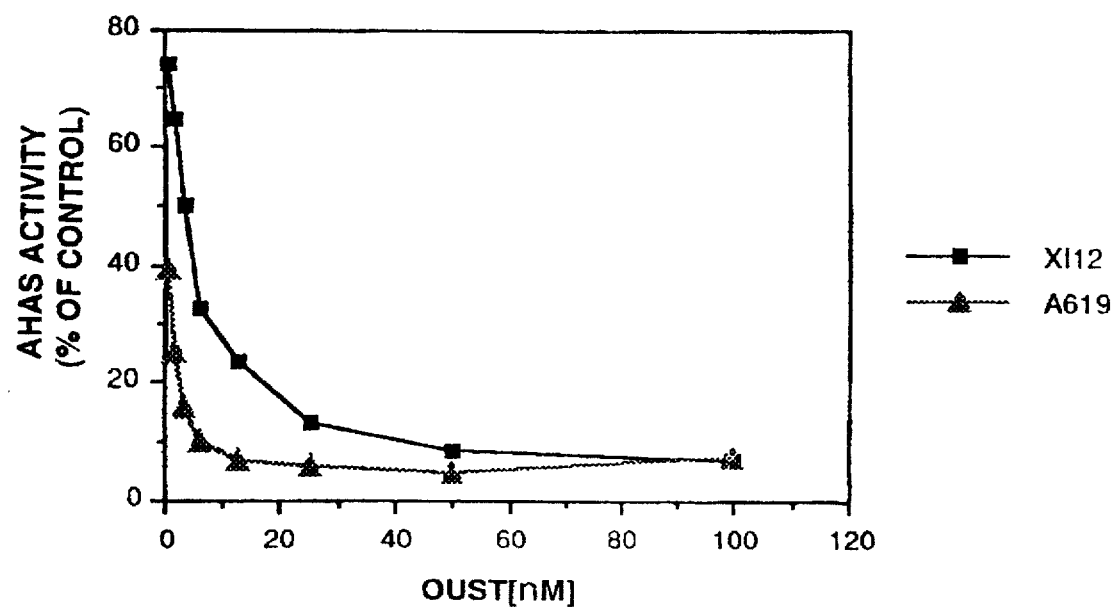

AHAS activity from B73, A619, or other wild-type maize lines is highly sensitive to inhibition by imazethapyr (PURSUIT™) with an $I_{50}$ of 1 uM (See FIG. 1). Contrary to this observation, XI12 shows 70–80% of enzyme activity at the highest concentrations (100 μM) of PURSUIT™ or ARSENAL™ (imazepyr), and about 70% in the presence of SCEPTER™ (imazequin). This result shows a 100-fold increase in tolerance of AHAS activity from XI12 to imazethapyr as compared to the in vitro AHAS activity from A619. Sensitivity of AHAS activity from the two lines to sulfonylureas gives a different picture. In the presence of OUST™ (sulfometuron methyl), at 100 nM, AHAS activity of XI12 is only 10–15%. AHAS activity of A619 in the presence of OUST™ IS 5–10%, and in the presence of PURSUIT™ is 15–20% (See FIG. 1).

3. Cloning of XI12 AHAS Genes

Seeds of the XI12 mutant derived from an imidazolinone resistant corn tissue culture line are planted; plants obtained therefrom appear to be segregating for the mutant AHAS phenotype. In order to obtain homozygous resistant seed material, a population of XI12 mutant plants are selfed. After selecting for herbicide resistance for three consecutive growing seasons, the seeds are homozygous for the mutant AHAS gene. Homozygous seeds are collected and used to grow seedlings to be used in AHAS gene isolation.

DNA is extracted from 7 days old etiolated seedlings of a homozygous XI12 line. 60 g of plant tissue is powdered in liquid nitrogen, and transferred into 108 ml DNA extraction buffer (1.4M NaCl, 2.0% Ctab (hexadecyl trimethyl ammonium bromide), 100 mM tris-Cl pH 8.0, 20 mM EDTA, 2% Mercaptoethanol) and 54 ml water. After incubation at 50°–60° C. for 30 minutes the suspension is extracted with an equal amount of chloroform. The DNA is precipitated by adding an equal amount of precipitation buffer (1% Ctab, 50 mM Tris-Cl pH 8.0, 10 mM EDTA). To purify the genomic DNA, a high speed centrifugation in 6.6M CsCl and ethidium bromide is performed (Ti80 rotor, 50,000 rpm, 20° C., 24 hours). The purified DNA is extracted with salt saturated Butanol and dialyzed for 25 hours against 3 changes of 1 l dialysis buffer (10 mM Tris-Cl Ph 8.0, 1 mM EDTA, 0.1M NaCl). The concentration of the XI12 genomic DNA is determined spectrophotometrically to be 310 mg/ml. The yield is 0.93 mg.

The XI12 genomic DNA is used to create a genomic library in the phage EMBL-3. The DNA is partially digested with MboI and the fragments are separated on a sucrose gradient to produce size range between 8 to 22 kb before cloning into the BamHI site of EMBL-3. After obtaining $2.1 \times 10^6$ independent clones, the library is amplified once. The titer of the library is determined $9 \times 10^{10}$ pfu/ml.

To obtain probes for analysis of the XI12 library, a W22 (wild-type) cDNA library in lambda gt11, purchased from Clontech Inc., California, is screened with an 800 nt BamH1 probe isolated from Arabidopsis AHAS genomic clone. The phages are plated in a density of 50,000 pfu/15 cm plate, transferred onto nitrocellulose filters, prehybridized in 6×SSC, 0.2% SDS for 2 hours and hybridized with the Arabidopsis AHAS probe in 6×SSC, 0.2% SDS overnight. One positive phage is identified, further purified and used for subcloning of a 1.1 kb EcoR1 fragment. The 1.1 kb EcoR1 fragment is subcloned into pGemA-4 and used as a probe to identify the XI12 AHAS genes.

Figure 2A:
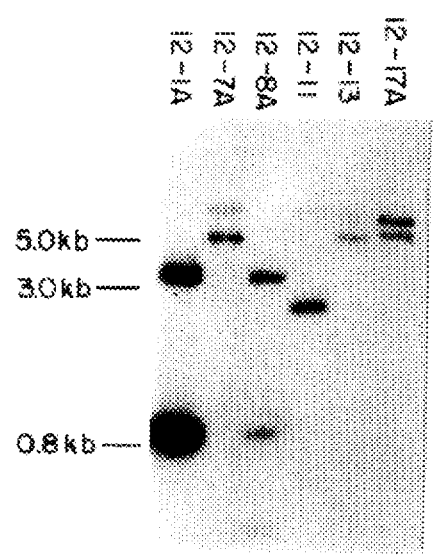
FIGS. 2A AND 2B: Southern analysis of genomic clones in phage EMBL3. Phages 12-1A (from W22), 12-7A, 18-8A, 12-11, and 12-17A (From XI12) are digested with XbaI or SalI, separated on a 1% agarose gel, transfered onto nitrocellulose and hybridized with an AHAS cDNA fragment as probe.
Figure 2B:
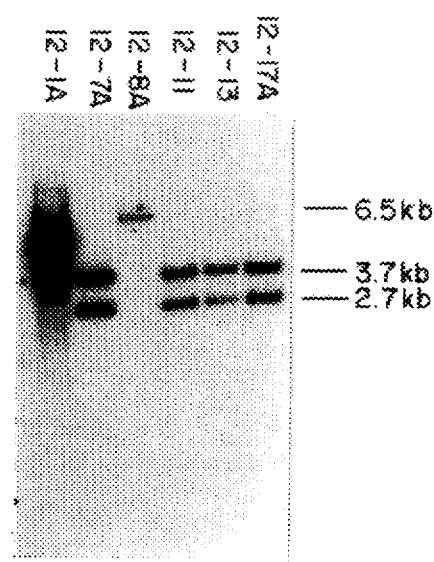
Figure 3:
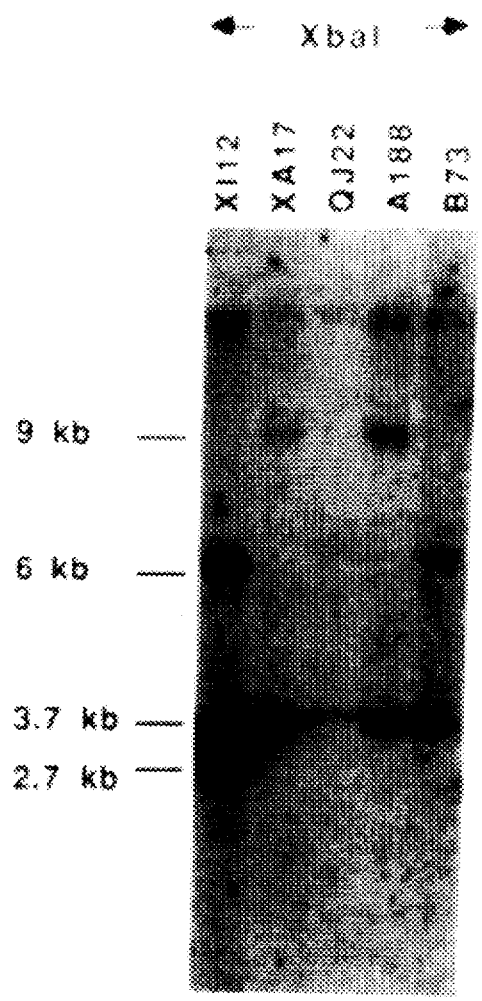
FIG. 3: Southern analysis of genomic DNA from corn lines XI12, XA17, QJ22, A188 and B73. The DNA is digested with XbaI, separated on a 1% agarose gel, transferred onto nitrocellulose and hybridized with an AHAS cDNA fragment as probe.

The XI12 genomic library is plated on 12 15-cm plates (concentration of 50,000 pfu/plate) and is screened with the W22 AHAS cDNA probe. The filters are prehybridized (2 hours) and hybridized (over night) in Church buffer (0.5 M Na Phosphate, 1 mM EDTA, 1% BSA, 7% SDS) at 65° C. and washed at 65° C. in 2×SSC, 0.2% SDS and 0.3 × SSC, 0.2% SDS. 12 positive plaques are obtained from a total of $7.5 \times 10^5$ pfu screened and 5 positive clones are further purified and isolated according to Chisholm (BioTechniques 7:21–23, 1989). Southern analysis (See FIG. 2) showed that the phage clones represented two types of AHAS clones: Type-1 clones contain one large Xbal (>6.5 kb) fragment hybridizing to the AHAS cDNA probe. Type-2 clones contained two 2.7 and 3.7 kb Xbal fragments hybridizing to the AHAS cDNA probe. Genomic Southern of XI12 DNA demonstrated, that the Xbal fragments obtained by digesting genomic DNA and by hybridizing to the AHAS cDNA probe correspond to the Xbal fragments identified in the XI12 phage clones (See FIG. 3) compared with other maize inbreds. Restriction digest and Southern Analysis also demonstrate that of the 5 AHAS clones, one clone represents the mutant als2 genes and four represent the als1 gene.

The AHAS genes corresponding to the mutant locus located on chromosome 5 (clone 12/8A) and the non-mutant locus located on chromosome 4 (clone 12/17A) are subcloned as a PstI fragment (clone 12/8A) or as Xbal fragment (12/17A) into the sequencing vector pBluescript II KSm13 (+) (pKS+; Stratagene). FIG 4 illustrates the restriction map of pCD8A containing the Pst1 fragment. Both 2.7 kb and 3.7 kb XbaI fragments from phage 12/17A contain one complete copy of AHAS genes which are identified. The sequence of each is obtained by dideoxy sequencing (Pharmacia T7 sequencing Kits) using primers complementary to the AHAS coding sequence.

The methods of DNA extraction, cloning of the genomic library and screening of the library are as described for the XI12 genomic DNA. The B73 AHAS genes are subcloned into the sequencing vector pKS+ as Xbal fragments and are sequenced. The sequence is obtained by dideoxy sequencing, using primers complementary to the AHAS coding sequence as described for the XI12 AHAS genes.

A W22 genomic library in EMBL3 purchased from Clontech Inc., California is screened. The phages are plated in a density of 50,000 pfu/7 inch plate, transferred onto nitrocellulose filters, and hybridized with the W22 AHAS cDNA probe described above (prehybridization and hybridization conditions: 6×SSC, 0.5% SDS, 1X Denhard's 100 mg/ml calf thymus DNA, 65° C., washing conditions: 3X×SSC, 0.2% SDS for 2 hours at 65° C., and 0.3×SSC, 0.2% SDS for 2 hours). Two positive phages (12/1A and 12/4—4) are identified and further purified.

The W22 genomic clone 12/1A is subcloned as two 0.78 kb (pGemA-4) and 3.0 kb (pGemA-14; Promega) SalI fragments into the vector pGem-A2, and as a 6.5 kb XbaI fragment into the vector pKS+ (pCD200). The coding strand sequence of the W22 AHAS gene is obtained by dideoxy sequencing of nested deletions created from subclones pGem A-14 and pGem A-4 of phage 12-1A. This sequence is used to design oligonucleotides complementary to the AHAS non-coding strand. The sequence of the non-coding strand is obtained by dideoxy sequencing of clone pCD200 using primers complementary to the coding strand. Upon complementing the sequencing of the W22 AHAS gene, primers of both DNA strands are designed and used for the sequencing of the AHAS genes isolated from the XI12 and B73 genomic libraries. (FIG. 5). The nucleotide and deduced amino acid sequences of mutant XI12 are depicted in FIG. 6.

RESULTS

The sequence of the mutant AHAS genes is compared with the sequences obtained from the wild type corn lines B73 and W22 (See FIG. 7). The XI12 mutant gene (XI12/8A) and the wild type gene are identical except for the amino acid change at position 621, causing a single nucleotide transition from AGT to AAT (See FIG. 8). The XI12 mutant XI12/8A and the wild-type B73/7-4 gene show two additional differences at positions 63 and 542. On the other hand, the non-mutant XI12 AHAS gene cloned in XI12/17A is completely homologous to the corresponding B73/10-2 in the region coding for the mature AHAS protein (data not shown).

DEPOSIT OF BIOLOGICAL MATERIALS

The following biological materials were deposited with the American Type Culture Collection, 12301 Parklawn Drive, Rockville, Md., 20857, as follows:

E. coli XLI Blue harboring plasmid pX12/8A, deposited on Jul. 3, 1991, Accession Number ATCC 68643

XI12 corn seed deposited on Jul. 16, 1991, Accession Number ATCC 75051.

---

What we claim is:

1. A nucleic acid from maize encoding a functional AHAS enzyme which has a serine-to-asparagine substitution at position 621 relative to the wild-type maize AHAS enzyme, which substitution confers imidazolinone resistance to the enzyme.

2. A transformation vector comprising the nucleic acid of claim 1.

3. A host cell comprising the nucleic acid sequence of claim 1.

4. A host cell comprising the vector of claim 2.

5. The host cell of claim 3 which is a plant cell or a bacterial cell.

6. The host cell of claim 4 which is a plant cell or a bacterial cell.

7. A method of conferring imidazolinone-specific resistance to a plant cell which comprises providing the plant cell with the nucleic acid sequence of claim 1.

8. A nucleic acid construct comprising the sequence of claim 1 linked to a gene encoding an agronomically useful trait.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:

( A ) LENGTH: 1969 BP's and 638 Amino Acids
        ( B ) TYPE: Nucleotide and Amino Acid
        ( C ) STRANDEDNESS: Single
        ( E ) TOPOLOGY: Linear ( i i ) MOLECULE TYPE: DNA and Protein ( x i ) SEQUENCE DESCRIPTION: SEQ ID NO: 1:

```
AACCCTCGCG CCGCCTCCGA GACAGCCGCC GCAACC                                    36

ATG GCC ACC GCC GCC GCC GCG TCT ACC GCG CTC ACT                            72
Met Ala Thr Ala Ala Ala Ala Ser Thr Ala Leu Thr
 1           5                   10

GGC GCC ACT ACC GCT GCG CCC AAG GCG AGG CGC CGG                           108
Gly Ala Thr Thr Ala Ala Pro Lys Ala Arg Arg Arg
         15                  20

GCG CAC CTC CTG GCC ACC CGC CGC GCC CTC GCC GCG                           144
Ala His Leu Leu Ala Thr Arg Arg Ala Leu Ala Ala
 25              30                      35

CCC ATC AGG TGC TCA GCG GCG TCA CCC GCC ATG CCG                           180
Pro Ile Arg Cys Ser Ala Ala Ser Pro Ala Met Pro
             40                  45

ATG GCT CCC CCG GCC ACC CCG CTC CGG CCG TGG GGC                           216
Met Ala Pro Pro Ala Thr Pro Leu Arg Pro Trp Gly
 50                      55                  60

CCC ACC GAT CCC CGC AAG GGC GCC GAC ATC CTC GTC                           252
Pro Thr Asp Pro Arg Lys Gly Ala Asp Ile Leu Val
                 65                  70

GAG TCC CTC GAG CGC TGC GGC GTC CGC GAC GTC TTC                           288
Glu Ser Leu Glu Arg Cys Gly Val Arg Asp Val Phe
         75                  80

GCC TAC CCC GGC GGC GCG TCC ATG GAG ATC CAC CAG                           324
Ala Tyr Pro Gly Gly Ala Ser Met Glu Ile His Gln
 85              90                      95

GCA CTC ACC CGC TCC CCC GTC ATC GCC AAC CAC CTC                           360
Ala Leu Thr Arg Ser Pro Val Ile Ala Asn His Leu
                100                 105

TTC CGC CAC GAG CAA GGG GAG GCC TTT GCG GCC TCC                           396
Phe Arg His Glu Gln Gly Glu Ala Phe Ala Ala Ser
        110                 115                 120

GGC TAC GCG CGC TCC TCG GGC CGC GTC GGC GTC TGC                           432
Gly Tyr Ala Arg Ser Ser Gly Arg Val Gly Val Cys
                125                 130

ATC GCC ACC TCC GGC CCC GGC GCC ACC AAC CTT GTC                           468
Ile Ala Thr Ser Gly Pro Gly Ala Thr Asn Leu Val
        135                 140

TCC GCG CTC GCC GAC GCG CTG CTC GAT TCC GTC CCC                           504
Ser Ala Leu Ala Asp Ala Leu Leu Asp Ser Val Pro
145                 150                 155

ATG GTC GCC ATC ACG GGA CAG GTG CCG CGA CGC ATG                           540
Met Val Ala Ile Thr Gly Gln Val Pro Arg Arg Met
                160                 165

ATT GGC ACC GAC GCC TTC CAG GAG ACG CCC ATC GTC                           576
Ile Gly Thr Asp Ala Phe Gln Glu Thr Pro Ile Val
        170                 175                 180

GAG GTC ACC CGC TCC ATC ACC AAG CAC AAC TAC CTG                           612
Glu Val Thr Arg Ser Ile Thr Lys His Asn Tyr Leu
                185                 190

GTC CTC GAC GTC GAC GAC ATC CCC CGC GTC GTG CAG                           648
Val Leu Asp Val Asp Asp Ile Pro Arg Val Val Gln
        195                 200

GAG GCT TTC TTC CTC GCC TCC TCT GGT CGA CCG GGG                           684
Glu Ala Phe Phe Leu Ala Ser Ser Gly Arg Pro Gly
205                 210                 215

CCG GTG CTT GTC GAC ATC CCC AAG GAC ATC CAG CAG                           720
Pro Val Leu Val Asp Ile Pro Lys Asp Ile Gln Gln
                220                 225

CAG ATG GCG GTG CCT GTC TGG GAC AAG CCC ATG AGT                           756
```

-continued

| | | | | | | | | | | | | |
|---|---|---|---|---|---|---|---|---|---|---|---|---|
| Gln | Met | Ala | Val | Pro | Val | Trp | Asp | Lys | Pro | Met | Ser | |
| | 230 | | | | 235 | | | | | | 240 | |
| CTG | CCT | GGG | TAC | ATT | GCG | CGC | CTT | CCC | AAG | CCC | CCT | 792 |
| Leu | Pro | Gly | Tyr | Ile | Ala | Arg | Leu | Pro | Lys | Pro | Pro | |
| | | | | 245 | | | | | 250 | | | |
| GCG | ACT | GAG | TTG | CTT | GAG | CAG | GTG | CTG | CGT | CTT | GTT | 828 |
| Ala | Thr | Glu | Leu | Leu | Glu | Gln | Val | Leu | Arg | Leu | Val | |
| | | 255 | | | | | 260 | | | | | |
| GGT | GAA | TCC | CGG | CGC | CCT | GTT | CTT | TAT | GTT | GGC | GGT | 864 |
| Gly | Glu | Ser | Arg | Arg | Pro | Val | Leu | Tyr | Val | Gly | Gly | |
| 265 | | | | | 270 | | | | | 275 | | |
| GCG | TGC | GCA | GCA | TCT | GGT | GAG | GAG | TTG | CGA | CGC | TTT | 900 |
| Ala | Cys | Ala | Ala | Ser | Gly | Glu | Glu | Leu | Arg | Arg | Phe | |
| | | | 280 | | | | | 285 | | | | |
| GTG | GAG | CTG | ACT | GGA | ATC | CCG | GTC | ACA | ACT | ACT | CTT | 936 |
| Val | Glu | Leu | Thr | Gly | Ile | Pro | Val | Thr | Thr | Thr | Leu | |
| | 290 | | | | | 295 | | | | | 300 | |
| ATG | GGC | CTC | GGC | AAC | TTC | CCC | AGC | GAC | GAC | CCA | CTG | 972 |
| Met | Gly | Leu | Gly | Asn | Phe | Pro | Ser | Asp | Asp | Pro | Leu | |
| | | | | 305 | | | | | 310 | | | |
| TCT | CTG | CGC | ATG | CTA | GGT | ATG | CAT | GGC | ACG | GTG | TAT | 1008 |
| Ser | Leu | Arg | Met | Leu | Gly | Met | His | Gly | Thr | Val | Tyr | |
| | | 315 | | | | | 320 | | | | | |
| GCA | AAT | TAT | GCA | GTG | GAT | AAG | GCC | GAT | CTG | TTG | CTT | 1044 |
| Ala | Asn | Tyr | Ala | Val | Asp | Lys | Ala | Asp | Leu | Leu | Leu | |
| 325 | | | | | 330 | | | | | 335 | | |
| GCA | CTT | GGT | GTG | CGG | TTT | GAT | GAT | CGT | GTG | ACA | GGG | 1080 |
| Ala | Leu | Gly | Val | Arg | Phe | Asp | Asp | Arg | Val | Thr | Gly | |
| | | | 340 | | | | | 345 | | | | |
| AAG | ATT | GAG | GCT | TTT | GCA | AGC | AGG | GCT | AAG | ATT | GTG | 1116 |
| Lys | Ile | Glu | Ala | Phe | Ala | Ser | Arg | Ala | Lys | Ile | Val | |
| | 350 | | | | | 355 | | | | | 360 | |
| CAC | GTT | GAT | ATT | GAT | CCG | GCT | GAG | ATT | GGC | AAG | AAC | 1152 |
| His | Val | Asp | Ile | Asp | Pro | Ala | Glu | Ile | Gly | Lys | Asn | |
| | | | | 365 | | | | | 370 | | | |
| AAG | CAG | CCA | CAT | GTG | TCC | ATC | TGT | GCA | GAT | GTT | AAG | 1188 |
| Lys | Gln | Pro | His | Val | Ser | Ile | Cys | Ala | Asp | Val | Lys | |
| | | 375 | | | | | 380 | | | | | |
| CTT | GCT | TTG | CAG | GGC | ATG | AAT | GCT | CTT | CTT | GAA | GGA | 1224 |
| Leu | Ala | Leu | Gln | Gly | Met | Asn | Ala | Leu | Leu | Glu | Gly | |
| 385 | | | | | 390 | | | | | 395 | | |
| AGC | ACA | TCA | AAG | AAG | AGC | TTT | GAC | TTT | GGC | TCA | TGG | 1260 |
| Ser | Thr | Ser | Lys | Lys | Ser | Phe | Asp | Phe | Gly | Ser | Trp | |
| | | | 400 | | | | | 405 | | | | |
| AAC | GAT | GAG | TTG | GAT | CAG | CAG | AAG | AGG | GAA | TTC | CCC | 1296 |
| Asn | Asp | Glu | Leu | Asp | Gln | Gln | Lys | Arg | Glu | Phe | Pro | |
| | 410 | | | | | 415 | | | | | 420 | |
| CTT | GGG | TAT | AAA | ACA | TCT | AAT | GAG | GAG | ATC | CAG | CCA | 1332 |
| Leu | Gly | Tyr | Lys | Thr | Ser | Asn | Glu | Glu | Ile | Gln | Pro | |
| | | | | 425 | | | | | 430 | | | |
| CAA | TAT | GCT | ATT | CAG | GTT | CTT | GAT | GAG | CTG | ACG | AAA | 1368 |
| Gln | Tyr | Ala | Ile | Gln | Val | Leu | Asp | Glu | Leu | Thr | Lys | |
| | | 435 | | | | | 440 | | | | | |
| GGC | GAG | GCC | ATC | ATC | GGC | ACA | GGT | GTT | GGG | CAG | CAC | 1404 |
| Gly | Glu | Ala | Ile | Ile | Gly | Thr | Gly | Val | Gly | Gln | His | |
| 445 | | | | | 450 | | | | | 455 | | |
| CAT | ATG | TGG | GCG | GCA | CAG | TAC | TAC | ACT | TAC | AAG | CGG | 1440 |
| Gln | Met | Trp | Ala | Ala | Gln | Tyr | Tyr | Thr | Tyr | Lys | Arg | |
| | | | 460 | | | | | 465 | | | | |
| CCA | AGG | CAG | TGG | TTG | TCT | TCA | GCT | GGT | CTT | GGG | GCT | 1476 |

```
        Pro  Arg  Gln  Trp  Leu  Ser  Ser  Ala  Gly  Leu  Gly  Ala
             470                 475                      480

ATG  GGA  TTT  GGT  TTG  CCG  GCT  GCT  GCT  GGT  GCT  TCT           1512
Met  Gly  Phe  Gly  Leu  Pro  Ala  Ala  Ala  Gly  Ala  Ser
               485                           490

GTG  GCC  AAC  CCA  GGT  GTT  ACT  GTT  GTT  GAC  ATC  GAT           1548
Val  Ala  Asn  Pro  Gly  Val  Thr  Val  Val  Asp  Ile  Asp
          495                      500

GGA  GAT  GGT  AGC  TTT  CTC  ATG  AAC  GTT  CAG  GAG  CTA           1584
Gly  Asp  Gly  Ser  Phe  Leu  Met  Asn  Val  Gln  Glu  Leu
505                      510                     515

GCT  ATG  ATC  CGA  ATT  GAG  AAC  CTC  CCG  GTG  AAG  GTC           1620
Ala  Met  Ile  Arg  Ile  Glu  Asn  Leu  Pro  Val  Lys  Val
               520                      525

TTT  GTG  CTA  AAC  AAC  CAG  CAC  CTG  GGG  ATG  GTG  GTG           1656
Phe  Val  Leu  Asn  Asn  Gln  His  Leu  Gly  Met  Val  Val
          530                      535                     540

CAG  TGG  GAG  GAC  AGG  TTC  TAT  AAG  GCC  AAC  AGA  GCG           1692
Gln  Trp  Glu  Asp  Arg  Phe  Tyr  Lys  Ala  Asn  Arg  Ala
                    545                      550

CAC  ACA  TAC  TTG  GGA  AAC  CCA  GAG  AAT  GAA  AGT  GAG           1728
His  Thr  Tyr  Leu  Gly  Asn  Pro  Glu  Asn  Glu  Ser  Glu
               555                      560

ATA  TAT  CCA  GAT  TTC  GTG  ACG  ATC  GCC  AAA  GGG  TTC           1764
Ile  Tyr  Pro  Asp  Phe  Val  Thr  Ile  Ala  Lys  Gly  Phe
565                      570                     575

AAC  ATT  CCA  GCG  GTC  CGT  GTG  ACA  AAG  AAG  AAC  GAA           1800
Asn  Ile  Pro  Ala  Val  Arg  Val  Thr  Lys  Lys  Asn  Glu
               580                      585

GTC  CGC  GCA  GCG  ATA  AAG  AAG  ATG  CTC  GAG  ACT  CCA           1836
Val  Arg  Ala  Ala  Ile  Lys  Lys  Met  Leu  Glu  Thr  Pro
          590                      595                     600

GGG  CCG  TAC  CTC  TTG  GAT  ATA  ATC  GTC  CCA  CAC  CAG           1872
Gly  Pro  Tyr  Leu  Leu  Asp  Ile  Ile  Val  Pro  His  Gln
                    605                      610

GAG  CAT  GTG  TTG  CCT  ATG  ATC  CCT  AAT  GGT  GGG  GCT           1908
Glu  His  Val  Leu  Pro  Met  Ile  Pro  Asn  Gly  Gly  Ala
               615                      620

TTC  AAG  GAT  ATG  ATC  CTG  GAT  GGT  GAT  GGC  AGG  ACT           1944
Phe  Lys  Asp  Met  Ile  Leu  Asp  Gly  Asp  Gly  Arg  Thr
625                      630                     635

GTG  TAC                                                             1950
Val  Tyr
638

TGATCTAAAA TCCAGCAAG                                                 1969

( 2 ) INFORMATION FOR SEQ ID NO: 2:

( i ) SEQUENCE CHARACTERISTICS:
                ( A ) LENGTH: 1969 BP's and 638 Amino Acids
                ( B ) TYPE: Nucleotide and Amino Acid
                ( C ) STRANDEDNESS: Single
                ( E ) TOPOLOGY: Linear ( i i ) MOLECULE TYPE: DNA and Protein ( x i ) SEQUENCE DESCRIPTION: SEQ ID NO: 2:

AACCCTCGCG  CCGCCTCCGA  GACAGCCGCC  GCAACC                            36

ATG  GCC  ACC  GCC  GCC  GCC  GCG  TCT  ACC  GCG  CTC  ACT            72
Met  Ala  Thr  Ala  Ala  Ala  Ala  Ser  Thr  Ala  Leu  Thr
1              5                        10
```

-continued

| | | | | | | | | | | | | |
|---|---|---|---|---|---|---|---|---|---|---|---|---|
| GGC | GCC | ACT | ACC | GCT | GCG | CCC | AAG | GCG | AGG | CGC | CGG | 108 |
| Gly | Ala | Thr | Thr | Ala | Ala | Pro | Lys | Ala | Arg | Arg | Arg | |
| | | 15 | | | | | 20 | | | | | |
| GCG | CAC | CTC | CTG | GCC | ACC | CGC | CGC | GCC | CTC | GCC | GCG | 144 |
| Ala | His | Leu | Leu | Ala | Thr | Arg | Arg | Ala | Leu | Ala | Ala | |
| 25 | | | | | 30 | | | | | 35 | | |
| CCC | ATC | AGG | TGC | TCA | GCG | GCG | TCA | CCC | GCC | ATG | CCG | 180 |
| Pro | Ile | Arg | Cys | Ser | Ala | Ala | Ser | Pro | Ala | Met | Pro | |
| | | | 40 | | | | | 45 | | | | |
| ATG | GCT | CCC | CCG | GCC | ACC | CCG | CTC | CGG | CCG | TGG | GGC | 216 |
| Met | Ala | Pro | Pro | Ala | Thr | Pro | Leu | Arg | Pro | Trp | Gly | |
| | | 50 | | | | 55 | | | | | 60 | |
| CCC | ACC | GAT | CCC | CGC | AAG | GGC | GCC | GAC | ATC | CTC | GTC | 252 |
| Pro | Thr | Asp | Pro | Arg | Lys | Gly | Ala | Asp | Ile | Leu | Val | |
| | | | | 65 | | | | | 70 | | | |
| GAG | TCC | CTC | GAG | CGC | TGC | GGC | GTC | CGC | GAC | GTC | TTC | 288 |
| Glu | Ser | Leu | Glu | Arg | Cys | Gly | Val | Arg | Asp | Val | Phe | |
| | | 75 | | | | | 80 | | | | | |
| GCC | TAC | CCC | GGC | GGC | GCG | TCC | ATG | GAG | ATC | CAC | CAG | 324 |
| Ala | Tyr | Pro | Gly | Gly | Ala | Ser | Met | Glu | Ile | His | Gln | |
| 85 | | | | | 90 | | | | | 95 | | |
| GCA | CTC | ACC | CGC | TCC | CCC | GTC | ATC | GCC | AAC | CAC | CTC | 360 |
| Ala | Leu | Thr | Arg | Ser | Pro | Val | Ile | Ala | Asn | His | Leu | |
| | | | 100 | | | | | 105 | | | | |
| TTC | CGC | CAC | GAG | CAA | GGG | GAG | GCC | TTT | GCG | GCC | TCC | 396 |
| Phe | Arg | His | Glu | Gln | Gly | Glu | Ala | Phe | Ala | Ala | Ser | |
| | | 110 | | | | 115 | | | | | 120 | |
| GGC | TAC | GCG | CGC | TCC | TCG | GGC | CGC | GTC | GGC | GTC | TGC | 432 |
| Gly | Tyr | Ala | Arg | Ser | Ser | Gly | Arg | Val | Gly | Val | Cys | |
| | | | | 125 | | | | 130 | | | | |
| ATC | GCC | ACC | TCC | GGC | CCC | GGC | GCC | ACC | AAC | CTT | GTC | 468 |
| Ile | Ala | Thr | Ser | Gly | Pro | Gly | Ala | Thr | Asn | Leu | Val | |
| | | 135 | | | | | 140 | | | | | |
| TCC | GCG | CTC | GCC | GAC | GCG | CTG | CTC | GAT | TCC | GTC | CCC | 504 |
| Ser | Ala | Leu | Ala | Asp | Ala | Leu | Leu | Asp | Ser | Val | Pro | |
| 145 | | | | | 150 | | | | | 155 | | |
| ATG | GTC | GCC | ATC | ACG | GGA | CAG | GTG | CCG | CGA | CGC | ATG | 540 |
| Met | Val | Ala | Ile | Thr | Gly | Gln | Val | Pro | Arg | Arg | Met | |
| | | | 160 | | | | | 165 | | | | |
| ATT | GGC | ACC | GAC | GCC | TTC | CAG | GAG | ACG | CCC | ATC | GTC | 576 |
| Ile | Gly | Thr | Asp | Ala | Phe | Gln | Glu | Thr | Pro | Ile | Val | |
| | 170 | | | | | 175 | | | | | 180 | |
| GAG | GTC | ACC | CGC | TCC | ATC | ACC | AAG | CAC | AAC | TAC | CTG | 612 |
| Glu | Val | Thr | Arg | Ser | Ile | Thr | Lys | His | Asn | Tyr | Leu | |
| | | | | 185 | | | | | 190 | | | |
| GTC | CTC | GAC | GTC | GAC | GAC | ATC | CCC | CGC | GTC | GTG | CAG | 648 |
| Val | Leu | Asp | Val | Asp | Asp | Ile | Pro | Arg | Val | Val | Gln | |
| | | 195 | | | | | 200 | | | | | |
| GAG | GCT | TTC | TTC | CTC | GCC | TCC | TCT | GGT | CGA | CCG | GGG | 684 |
| Glu | Ala | Phe | Phe | Leu | Ala | Ser | Ser | Gly | Arg | Pro | Gly | |
| 205 | | | | | 210 | | | | | 215 | | |
| CCG | GTG | CTT | GTC | GAC | ATC | CCC | AAG | GAC | ATC | CAG | CAG | 720 |
| Pro | Val | Leu | Val | Asp | Ile | Pro | Lys | Asp | Ile | Gln | Gln | |
| | | | 220 | | | | | 225 | | | | |
| CAG | ATG | GCG | GTG | CCT | GTC | TGG | GAC | AAG | CCC | ATG | AGT | 756 |
| Gln | Met | Ala | Val | Pro | Val | Trp | Asp | Lys | Pro | Met | Ser | |
| | 230 | | | | | 235 | | | | | 240 | |
| CTG | CCT | GGG | TAC | ATT | GCG | CGC | CTT | CCC | AAG | CCC | CCT | 792 |
| Leu | Pro | Gly | Tyr | Ile | Ala | Arg | Leu | Pro | Lys | Pro | Pro | |
| | | | | 245 | | | | | 250 | | | |

| | | | | | | | | | | | |
|---|---|---|---|---|---|---|---|---|---|---|---|
| GCG | ACT | GAG | TTG | CTT | GAG | CAG | GTG | CTG | CGT | CTT | GTT | 828 |
| Ala | Thr | Glu | Leu | Leu | Glu | Gln | Val | Leu | Arg | Leu | Val | |
| | | 255 | | | | 260 | | | | | | |
| GGT | GAA | TCC | CGG | CGC | CCT | GTT | CTT | TAT | GTT | GGC | GGT | 864 |
| Gly | Glu | Ser | Arg | Arg | Pro | Val | Leu | Tyr | Val | Gly | Gly | |
| 265 | | | | 270 | | | | | 275 | | | |
| GCG | TGC | GCA | GCA | TCT | GGT | GAG | GAG | TTG | CGA | CGC | TTT | 900 |
| Ala | Cys | Ala | Ala | Ser | Gly | Glu | Glu | Leu | Arg | Arg | Phe | |
| | | | 280 | | | | | 285 | | | | |
| GTG | GAG | CTG | ACT | GGA | ATC | CCG | GTC | ACA | ACT | ACT | CTT | 936 |
| Val | Glu | Leu | Thr | Gly | Ile | Pro | Val | Thr | Thr | Thr | Leu | |
| | 290 | | | | | 295 | | | | | 300 | |
| ATG | GGC | CTC | GGC | AAC | TTC | CCC | AGC | GAC | GAC | CCA | CTG | 972 |
| Met | Gly | Leu | Gly | Asn | Phe | Pro | Ser | Asp | Asp | Pro | Leu | |
| | | | | 305 | | | | | 310 | | | |
| TCT | CTG | CGC | ATG | CTA | GGT | ATG | CAT | GGC | ACG | GTG | TAT | 1008 |
| Ser | Leu | Arg | Met | Leu | Gly | Met | His | Gly | Thr | Val | Tyr | |
| | | 315 | | | | | 320 | | | | | |
| GCA | AAT | TAT | GCA | GTG | GAT | AAG | GCC | GAT | CTG | TTG | CTT | 1044 |
| Ala | Asn | Tyr | Ala | Val | Asp | Lys | Ala | Asp | Leu | Leu | Leu | |
| 325 | | | | | 330 | | | | | 335 | | |
| GCA | CTT | GGT | GTG | CGG | TTT | GAT | GAT | CGT | GTG | ACA | GGG | 1080 |
| Ala | Leu | Gly | Val | Arg | Phe | Asp | Asp | Arg | Val | Thr | Gly | |
| | | | 340 | | | | | 345 | | | | |
| AAG | ATT | GAG | GCT | TTT | GCA | AGC | AGG | GCT | AAG | ATT | GTG | 1116 |
| Lys | Ile | Glu | Ala | Phe | Ala | Ser | Arg | Ala | Lys | Ile | Val | |
| | | 350 | | | | | 355 | | | | 360 | |
| CAC | GTT | GAT | ATT | GAT | CCG | GCT | GAG | ATT | GGC | AAG | AAC | 1152 |
| His | Val | Asp | Ile | Asp | Pro | Ala | Glu | Ile | Gly | Lys | Asn | |
| | | | | 365 | | | | | 370 | | | |
| AAG | CAG | CCA | CAT | GTG | TCC | ATC | TGT | GCA | GAT | GTT | AAG | 1188 |
| Lys | Gln | Pro | His | Val | Ser | Ile | Cys | Ala | Asp | Val | Lys | |
| | | 375 | | | | | 380 | | | | | |
| CTT | GCT | TTG | CAG | GGC | ATG | AAT | GCT | CTT | CTT | GAA | GGA | 1224 |
| Leu | Ala | Leu | Gln | Gly | Met | Asn | Ala | Leu | Leu | Glu | Gly | |
| 385 | | | | | 390 | | | | | 395 | | |
| AGC | ACA | TCA | AAG | AAG | AGC | TTT | GAC | TTT | GGC | TCA | TGG | 1260 |
| Ser | Thr | Ser | Lys | Lys | Ser | Phe | Asp | Phe | Gly | Ser | Trp | |
| | | | 400 | | | | | 405 | | | | |
| AAC | GAT | GAG | TTG | GAT | CAG | CAG | AAG | AGG | GAA | TTC | CCC | 1296 |
| Asn | Asp | Glu | Leu | Asp | Gln | Gln | Lys | Arg | Glu | Phe | Pro | |
| | 410 | | | | | 415 | | | | | 420 | |
| CTT | GGG | TAT | AAA | ACA | TCT | AAT | GAG | GAG | ATC | CAG | CCA | 1332 |
| Leu | Gly | Tyr | Lys | Thr | Ser | Asn | Glu | Glu | Ile | Gln | Pro | |
| | | | | 425 | | | | | 430 | | | |
| CAA | TAT | GCT | ATT | CAG | GTT | CTT | GAT | GAG | CTG | ACG | AAA | 1368 |
| Gln | Tyr | Ala | Ile | Gln | Val | Leu | Asp | Glu | Leu | Thr | Lys | |
| | | | 435 | | | | | 440 | | | | |
| GGC | GAG | GCC | ATC | ATC | GGC | ACA | GGT | GTT | GGG | CAG | CAC | 1404 |
| Gly | Glu | Ala | Ile | Ile | Gly | Thr | Gly | Val | Gly | Gln | His | |
| 445 | | | | | 450 | | | | | 455 | | |
| CAT | ATG | TGG | GCG | GCA | CAG | TAC | TAC | ACT | TAC | AAG | CGG | 1440 |
| Gln | Met | Trp | Ala | Ala | Gln | Tyr | Tyr | Thr | Tyr | Lys | Arg | |
| | | | | 460 | | | | | 465 | | | |
| CCA | AGG | CAG | TGG | TTG | TCT | TCA | GCT | GGT | CTT | GGG | GCT | 1476 |
| Pro | Arg | Gln | Trp | Leu | Ser | Ser | Ala | Gly | Leu | Gly | Ala | |
| | | 470 | | | | | 475 | | | | 480 | |
| ATG | GGA | TTT | GGT | TTG | CCG | GCT | GCT | GCT | GGT | GCT | TCT | 1512 |
| Met | Gly | Phe | Gly | Leu | Pro | Ala | Ala | Ala | Gly | Ala | Ser | |
| | | | | 485 | | | | | 490 | | | |

-continued

| | | | | | | | | | | | |
|---|---|---|---|---|---|---|---|---|---|---|---|
| GTG | GCC | AAC | CCA | GGT | GTT | ACT | GTT | GTT | GAC | ATC | GAT | 1548 |
| Val | Ala | Asn | Pro | Gly | Val | Thr | Val | Val | Asp | Ile | Asp |
| | | 495 | | | | 500 | | | | | |

| GGA | GAT | GGT | AGC | TTT | CTC | ATG | AAC | GTT | CAG | GAG | CTA | 1584 |
| Gly | Asp | Gly | Ser | Phe | Leu | Met | Asn | Val | Gln | Glu | Leu |
| 505 | | | | | 510 | | | | | 515 | |

| GCT | ATG | ATC | CGA | ATT | GAG | AAC | CTC | CCG | GTG | AAG | GTC | 1620 |
| Ala | Met | Ile | Arg | Ile | Glu | Asn | Leu | Pro | Val | Lys | Val |
| | | | 520 | | | | | 525 | | | |

| TTT | GTG | CTA | AAC | AAC | CAG | CAC | CTG | GGG | ATG | GTG | GTG | 1656 |
| Phe | Val | Leu | Asn | Asn | Gln | His | Leu | Gly | Met | Val | Val |
| | 530 | | | | | 535 | | | | | 540 |

| CAG | TGG | GAG | GAC | AGG | TTC | TAT | AAG | GCC | AAC | AGA | GCG | 1692 |
| Gln | Trp | Glu | Asp | Arg | Phe | Tyr | Lys | Ala | Asn | Arg | Ala |
| | | | | 545 | | | | | 550 | | |

| CAC | ACA | TAC | TTG | GGA | AAC | CCA | GAG | AAT | GAA | AGT | GAG | 1728 |
| His | Thr | Tyr | Leu | Gly | Asn | Pro | Glu | Asn | Glu | Ser | Glu |
| | | 555 | | | | | 560 | | | | |

| ATA | TAT | CCA | GAT | TTC | GTG | ACG | ATC | GCC | AAA | GGG | TTC | 1764 |
| Ile | Tyr | Pro | Asp | Phe | Val | Thr | Ile | Ala | Lys | Gly | Phe |
| 565 | | | | | 570 | | | | | 575 | |

| AAC | ATT | CCA | GCG | GTC | CGT | GTG | ACA | AAG | AAG | AAC | GAA | 1800 |
| Asn | Ile | Pro | Ala | Val | Arg | Val | Thr | Lys | Lys | Asn | Glu |
| | | | 580 | | | | | 585 | | | |

| GTC | CGC | GCA | GCG | ATA | AAG | AAG | ATG | CTC | GAG | ACT | CCA | 1836 |
| Val | Arg | Ala | Ala | Ile | Lys | Lys | Met | Leu | Glu | Thr | Pro |
| | 590 | | | | | 595 | | | | | 600 |

| GGG | CCG | TAC | CTC | TTG | GAT | ATA | ATC | GTC | CCA | CAC | CAG | 1872 |
| Gly | Pro | Tyr | Leu | Leu | Asp | Ile | Ile | Val | Pro | His | Gln |
| | | | | 605 | | | | | 610 | | |

| GAG | CAT | GTG | TTG | CCT | ATG | ATC | CCT | AGT | GGT | GGG | GCT | 1908 |
| Glu | His | Val | Leu | Pro | Met | Ile | Pro | Ser | Gly | Gly | Ala |
| | | 615 | | | | | 620 | | | | |

| TTC | AAG | GAT | ATG | ATC | CTG | GAT | GGT | GAT | GGC | AGG | ACT | 1944 |
| Phe | Lys | Asp | Met | Ile | Leu | Asp | Gly | Asp | Gly | Arg | Thr |
| 625 | | | | | 630 | | | | | 635 | |

| GTG | TAC | | | | | | | | | | | 1950 |
| Val | Tyr |
| | 638 |

TGATCTAAAA TCCAGCAAG  1969

( 2 ) INFORMATION FOR SEQ ID NO: 3:

( i ) SEQUENCE CHARACTERISTICS:
        ( A ) LENGTH: 1969 BP's and 638 Amino Acids
        ( B ) TYPE: Nucleotide and Amino Acid
        ( C ) STRANDEDNESS: Single
        ( E ) TOPOLOGY: Linear ( i i ) MOLECULE TYPE: DNA and Protein ( x i ) SEQUENCE DESCRIPTION: SEQ ID NO: 3:

AACCCTCGCG CCGCCTCCGA GACAGCCGCC GCAACC  36

| ATG | GCC | ACC | GCC | GCC | GCC | GCG | TCT | ACC | GCG | CTC | ACT | 72 |
|---|---|---|---|---|---|---|---|---|---|---|---|---|
| Met | Ala | Thr | Ala | Ala | Ala | Ala | Ser | Thr | Ala | Leu | Thr |
| 1 | | | | 5 | | | | | | 10 | |

| GGC | GCC | ACT | ACC | GCT | GCG | CCC | AAG | GCG | AGG | CGC | CGG | 108 |
| Gly | Ala | Thr | Thr | Ala | Ala | Pro | Lys | Ala | Arg | Arg | Arg |
| | | 15 | | | | | 20 | | | | |

| GCG | CAC | CTC | CTG | GCC | ACC | CGC | CGC | GCC | CTC | GCC | GCG | 144 |
| Ala | His | Leu | Leu | Ala | Thr | Arg | Arg | Ala | Leu | Ala | Ala |
| 25 | | | | | 30 | | | | | 35 | |

```
CCC ATC AGG TGC TCA GCG GCG TCA CCC GCC ATG CCG      180
Pro Ile Arg Cys Ser Ala Ala Ser Pro Ala Met Pro
            40                  45

ATG GCT CCC CCG GCC ACC CCG CTC CGG CCG TGG GGC      216
Met Ala Pro Pro Ala Thr Pro Leu Arg Pro Trp Gly
        50                  55                  60

CCC ACC GAG CCC CGC AAG GGT GCT GAC ATC CTC GTC      252
Pro Thr Glu Pro Arg Lys Gly Ala Asp Ile Leu Val
                    65                  70

GAG TCC CTC GAG CGC TGC GGC GTC CGC GAC GTC TTC      288
Glu Ser Leu Glu Arg Cys Gly Val Arg Asp Val Phe
            75                  80

GCC TAC CCC GGC GGC GCG TCC ATG GAG ATC CAC CAG      324
Ala Tyr Pro Gly Gly Ala Ser Met Glu Ile His Gln
 85                  90                  95

GCA CTC ACC CGC TCC CCC GTC ATC GCC AAC CAC CTC      360
Ala Leu Thr Arg Ser Pro Val Ile Ala Asn His Leu
            100                 105

TTC CGC CAC GAG CAA GGG GAG GCC TTT GCC GCC TCC      396
Phe Arg His Glu Gln Gly Glu Ala Phe Ala Ala Ser
    110                 115                 120

GGC TAC GCG CGC TCC TCG GGC CGC GTC GGC GTC TGC      432
Gly Tyr Ala Arg Ser Ser Gly Arg Val Gly Val Cys
                125                 130

ATC GCC ACC TCC GGC CCC GGC GCC ACC AAC CTA GTC      468
Ile Ala Thr Ser Gly Pro Gly Ala Thr Asn Leu Val
            135                 140

TCC GCG CTC GCC GAC GCG CTG CTC GAT TCC GTC CCC      504
Ser Ala Leu Ala Asp Ala Leu Leu Asp Ser Val Pro
145                 150                 155

ATG GTC GCC ATC ACG GGA CAG GTG CCG CGA CGC ATG      540
Met Val Ala Ile Thr Gly Gln Val Pro Arg Arg Met
            160                 165

ATT GGC ACC GAC GCC TTC CAG GAG ACG CCC ATC GTC      576
Ile Gly Thr Asp Ala Phe Gln Glu Thr Pro Ile Val
    170                 175                 180

GAG GTC ACC CGC TCC ATC ACC AAG CAC AAC TAC CTG      612
Glu Val Thr Arg Ser Ile Thr Lys His Asn Tyr Leu
                185                 190

GTC CTC GAC GTC GAC GAC ATC CCC CGC GTC GTG CAG      648
Val Leu Asp Val Asp Asp Ile Pro Arg Val Val Gln
            195                 200

GAG GCT TTC TTC CTC GCC TCC TCT GGT CGA CCA GGG      684
Glu Ala Phe Phe Leu Ala Ser Ser Gly Arg Pro Gly
205                 210                 215

CCG GTG CTT GTC GAC ATC CCC AAG GAC ATC CAG CAG      720
Pro Val Leu Val Asp Ile Pro Lys Asp Ile Gln Gln
            220                 225

CAG ATG GCG GTG CCT GTC TGG GAC AAG CCC ATG AGT      756
Gln Met Ala Val Pro Val Trp Asp Lys Pro Met Ser
    230                 235                 240

CTG CCT GGG TAC ATT GCG CGC CTT CCC AAG CCC CCT      792
Leu Pro Gly Tyr Ile Ala Arg Leu Pro Lys Pro Pro
                245                 250

GCG ACT GAG TTG CTT GAG CAG GTG CTG CGT CTT GTT      828
Ala Thr Glu Leu Leu Glu Gln Val Leu Arg Leu Val
            255                 260

GGT GAA TCG CGG CGC CCT GTT CTT TAT GTG GGC GGT      864
Gly Glu Ser Arg Arg Pro Val Leu Tyr Val Gly Gly
265                 270                 275
```

```
GCG TGC GCA GCA TCT GGT GAG GAG TTG CGA CGC TTT       900
Ala Cys Ala Ala Ser Gly Glu Glu Leu Arg Arg Phe
        280                 285

GTG GAG CTG ACT GGA ATC CCG GTC ACA ACT ACT CTT       936
Val Glu Leu Thr Gly Ile Pro Val Thr Thr Thr Leu
    290                 295                 300

ATG GGC CTC GGC AAC TTC CCC AGC GAC GAC CCA CTG       972
Met Gly Leu Gly Asn Phe Pro Ser Asp Asp Pro Leu
                305                 310

TCT CTG CGC ATG CTA GGT ATG CAT GGG ACG GTG TAT      1008
Ser Leu Arg Met Leu Gly Met His Gly Thr Val Tyr
        315                 320

GCA AAT TAT GCA GTG GAT AAG GCC GAT CTG TTG CTT      1044
Ala Asn Tyr Ala Val Asp Lys Ala Asp Leu Leu Leu
325                 330                 335

GCA CTT GGT GTG CGG TTT GAT GAT CGT GTG ACA GGG      1080
Ala Leu Gly Val Arg Phe Asp Asp Arg Val Thr Gly
            340                 345

AAG ATT GAG GCT TTT GCA AGC AGG GCT AAG ATT GTG      1116
Lys Ile Glu Ala Phe Ala Ser Arg Ala Lys Ile Val
    350                 355                 360

CAC GTT GAT ATT GAT CCG GCT GAG ATT GGC AAG AAC      1152
His Val Asp Ile Asp Pro Ala Glu Ile Gly Lys Asn
                365                 370

AAG CAG CCA CAT GTG TCC ATC TGT GCA GAT GTT AAG      1188
Lys Gln Pro His Val Ser Ile Cys Ala Asp Val Lys
        375                 380

CTT GCT TTG CAG GGC ATG AAT GCT CTT CTT GAA GGA      1224
Leu Ala Leu Gln Gly Met Asn Ala Leu Leu Glu Gly
385                 390                 395

AGC ACA TCA AAG AAG AGC TTT GAC TTT GGC TCA TGG      1260
Ser Thr Ser Lys Lys Ser Phe Asp Phe Gly Ser Trp
            400                 405

AAC GAT GAG TTG GAT CAG CAG AAG AGG GAA TTC CCC      1296
Asn Asp Glu Leu Asp Gln Gln Lys Arg Glu Phe Pro
    410                 415                 420

CTT GGG TAT AAA ACA TCT AAT GAG GAG ATC CAG CCA      1332
Leu Gly Tyr Lys Thr Ser Asn Glu Glu Ile Gln Pro
                425                 430

CAA TAT GCT ATT CAG GTT CTT GAT GAG CTG ACG AAA      1368
Gln Tyr Ala Ile Gln Val Leu Asp Glu Leu Thr Lys
        435                 440

GGC GAG GCC ATC ATC GGC ACA GGT GTT GGG CAG CAC      1404
Gly Glu Ala Ile Ile Gly Thr Gly Val Gly Gln His
445                 450                 455

CAT ATG TGG GCG GCA CAG TAC TAC ACT TAC AAG CGG      1440
Gln Met Trp Ala Ala Gln Tyr Tyr Thr Tyr Lys Arg
            460                 465

CCA AGG CAG TGG TTG TCT TCA GCT GGT CTT GGG GCT      1476
Pro Arg Gln Trp Leu Ser Ser Ala Gly Leu Gly Ala
    470                 475                 480

ATG GGA TTT GGT TTG CCG GCT GCT GCT GGT GCT TCT      1512
Met Gly Phe Gly Leu Pro Ala Ala Ala Gly Ala Ser
                485                 490

GTG GCC AAC CCA GGT GTC ACT GTT GTT GAC ATC GAT      1548
Val Ala Asn Pro Gly Val Thr Val Val Asp Ile Asp
        495                 500

GGA GAT GGT AGC TTT CTC ATG AAC GTT CAG GAG CTA      1584
Gly Asp Gly Ser Phe Leu Met Asn Val Gln Glu Leu
505                 510                 515
```

```
GCT ATG ATC CGA ATT GAG AAC CTC CCA GTG AAG GTC          1620
Ala Met Ile Arg Ile Glu Asn Leu Pro Val Lys Val
            520                 525

TTT GTG CTA AAC AAC CAG CAC CTG GGG ATG GTG GTG          1656
Phe Val Leu Asn Asn Gln His Leu Gly Met Val Val
    530             535                     540

CAG TTG GAG GAC AGG TTC TAT AAG GCC AAC AGA GCG          1692
Gln Leu Glu Asp Arg Phe Tyr Lys Ala Asn Arg Ala
                545             550

CAC ACA TAC TTG GGA AAC CCA GAG AAT GAA AGT GAG          1728
His Thr Tyr Leu Gly Asn Pro Glu Asn Glu Ser Glu
        555                 560

ATA TAT CCA GAT TTC GTG ACG ATC GCC AAA GGG TTC          1764
Ile Tyr Pro Asp Phe Val Thr Ile Ala Lys Gly Phe
565                 570                 575

AAC ATT CCA GCG GTC CGT GTG ACA AAG AAG AAC GAA          1800
Asn Ile Pro Ala Val Arg Val Thr Lys Lys Asn Glu
            580                 585

GTC CGC GCA GCG ATA AAG AAG ATG CTC GAG ACT CCA          1836
Val Arg Ala Ala Ile Lys Lys Met Leu Glu Thr Pro
    590                 595                 600

GGG CCG TAC CTC TTG GAT ATA ATC GTC CCA CAC CAG          1872
Gly Pro Tyr Leu Leu Asp Ile Ile Val Pro His Gln
                605                 610

GAG CAT GTG TTG CCT ATG ATC CCT AGT GGT GGG GCT          1908
Glu His Val Leu Pro Met Ile Pro Ser Gly Gly Ala
        615                 620

TTC AAG GAT ATG ATC CTG GAT GGT GAT GGC AGG ACT          1944
Phe Lys Asp Met Ile Leu Asp Gly Asp Gly Arg Thr
625                 630                 635

GTG TAC                                                  1950
Val Tyr
638

TGATCTAAAA TCCAGCAAG                                     1969
```